US011883824B2

(12) United States Patent
Chou et al.

(10) Patent No.: US 11,883,824 B2
(45) Date of Patent: *Jan. 30, 2024

(54) ASSAY USING DIFFERENT SPACING HEIGHTS

(71) Applicant: Essenlix Corporation, Monmouth Junction, NJ (US)

(72) Inventors: Stephen Y. Chou, Princeton, NJ (US); Wei Ding, East Windsor, NJ (US); Ji Qi, Lawrence Township, NJ (US); Yufan Zhang, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/081,970

(22) PCT Filed: Feb. 9, 2018

(86) PCT No.: PCT/US2018/017713
§ 371 (c)(1),
(2) Date: Sep. 4, 2018

(87) PCT Pub. No.: WO2018/148607
PCT Pub. Date: Aug. 16, 2018

(65) Prior Publication Data
US 2019/0111424 A1 Apr. 18, 2019

Related U.S. Application Data

(60) Provisional application No. 62/577,370, filed on Oct. 26, 2017, provisional application No. 62/539,718, (Continued)

(51) Int. Cl.
*B01L 3/00* (2006.01)
*G01N 21/84* (2006.01)
(Continued)

(52) U.S. Cl.
CPC ......... *B01L 3/50853* (2013.01); *B01L 3/5088* (2013.01); *G01N 21/03* (2013.01);
(Continued)

(58) Field of Classification Search
None
See application file for complete search history.

(56) References Cited

U.S. PATENT DOCUMENTS 3,368,872 A 2/1968 Natelson
3,447,863 A 6/1969 Patterson
(Continued)

FOREIGN PATENT DOCUMENTS

AU 198813789 A 9/1988
AU 619459 B 1/1992
(Continued)

OTHER PUBLICATIONS

Van Vliet, Dillys et al., Prediction of asthma exacerbations in children by innovative exhaled inflammatory markers: Results of a longitudinal study, Plos One, Mar. 23, 2015.
(Continued)

*Primary Examiner* — Liban M Hassan

(57) ABSTRACT

Disclosure relates to a device and a method of using the device for conducting biological and chemical assays on a sample. The device includes two plates. The first plate includes at least a first and a second sample contact areas on its inner surface. Each sample contact area includes spacers having a bottom end fixed on the inner surface and a top end that is distal to the inner surface. The spacers in the first sample contact area differ in height from those in the second sample contact area. The first and second sample contact areas are disposed at different depths along the inner surface of the first plate, so that the top ends of the spacers are aligned on the same flat plane. The method includes depos-
(Continued)

iting the sample onto the sample contact areas, compressing the sample into a thin layer, and analyzing the sample.

48 Claims, 10 Drawing Sheets

Related U.S. Application Data filed on Aug. 1, 2017, provisional application No. 62/457,133, filed on Feb. 9, 2017.

(51) Int. Cl.
*G01N 33/543* (2006.01)
*G01N 21/03* (2006.01)

(52) U.S. Cl.
CPC ........... *G01N 21/84* (2013.01); *G01N 33/543* (2013.01); *G01N 33/54366* (2013.01); *B01L 2300/04* (2013.01); *B01L 2300/0609* (2013.01); *B01L 2300/0829* (2013.01); *B01L 2300/0851* (2013.01); *B01L 2300/0861* (2013.01)

(56) References Cited

U.S. PATENT DOCUMENTS

| | | | |
|---|---|---|---|
| 3,895,661 | A | 7/1975 | Praglin et al. |
| 3,925,166 | A | 12/1975 | Blume |
| 3,992,158 | A | 11/1976 | Przybylowicz et al. |
| 4,022,521 | A | 5/1977 | Hall et al. |
| 4,066,412 | A | 1/1978 | Johnson et al. |
| 4,088,448 | A | 5/1978 | Lilja et al. |
| 4,171,866 | A | 10/1979 | Tolles |
| 4,233,029 | A | 11/1980 | Columbus |
| 4,255,384 | A | 3/1981 | Kitajima et al. |
| 4,258,001 | A | 3/1981 | Pierce et al. |
| 4,329,054 | A | 5/1982 | Bachalo |
| 4,402,614 | A | 9/1983 | Porath-Furedi |
| 4,427,294 | A | 1/1984 | Pietro |
| 4,430,436 | A | 2/1984 | Koyama et al. |
| 4,596,695 | A | 6/1986 | Cottingham |
| 4,745,075 | A | 5/1988 | Hadfield et al. |
| 4,806,311 | A | 2/1989 | Greenquist |
| 4,883,642 | A | 11/1989 | Bisconte |
| 4,906,439 | A | 3/1990 | Grenner |
| 4,911,782 | A | 3/1990 | Brown |
| 4,950,455 | A | 8/1990 | Smith |
| 5,002,736 | A | 3/1991 | Babbitt et al. |
| 5,039,487 | A | 8/1991 | Smith |
| 5,096,836 | A | 3/1992 | Macho et al. |
| 5,122,284 | A | 6/1992 | Braynin et al. |
| 5,132,097 | A | 7/1992 | Van Deusen et al. |
| 5,169,601 | A | 12/1992 | Ohta et al. |
| 5,188,968 | A | 2/1993 | Kano et al. |
| 5,223,219 | A | 6/1993 | Subramanian et al. |
| 5,281,540 | A | 1/1994 | Merkh et al. |
| 5,306,467 | A | 4/1994 | Douglas-Hamilton et al. |
| 5,321,975 | A | 6/1994 | Wardlaw |
| 5,362,648 | A | 11/1994 | Koreyasu et al. |
| 5,413,732 | A | 5/1995 | Buhl et al. |
| 5,427,959 | A | 6/1995 | Nishimura et al. |
| 5,431,880 | A | 7/1995 | Kramer |
| 5,591,403 | A | 1/1997 | Gavin et al. |
| 5,623,415 | A | 4/1997 | O'Bryan et al. |
| 5,753,456 | A | 5/1998 | Naqui et al. |
| 5,768,407 | A | 6/1998 | Shen et al. |
| 5,858,648 | A | 1/1999 | Steel et al. |
| 5,879,628 | A | 3/1999 | Ridgeway et al. |
| 5,888,834 | A | 3/1999 | Ishikawa et al. |
| 5,939,326 | A | 8/1999 | Chupp et al. |
| 5,948,686 | A | 9/1999 | Wardlaw |
| 6,004,821 | A | 12/1999 | Levine et al. |
| 6,016,367 | A | 1/2000 | Benedetti et al. |
| 6,017,767 | A | 1/2000 | Chandler |
| 6,022,734 | A | 2/2000 | Wardlaw |
| 6,083,761 | A | 7/2000 | Kedar et al. |
| 6,106,778 | A | 8/2000 | Oku et al. |
| 6,180,314 | B1 | 1/2001 | Berndt |
| 6,235,536 | B1 | 5/2001 | Wardlaw |
| 6,350,613 | B1 | 2/2002 | Wardlaw et al. |
| 6,358,475 | B1 | 3/2002 | Berndt |
| 6,429,027 | B1 | 8/2002 | Chee et al. |
| 6,503,760 | B2 | 1/2003 | Malmqvist et al. |
| 6,551,554 | B1 | 4/2003 | Vermeiden et al. |
| 6,623,701 | B1 | 9/2003 | Eichele et al. |
| 6,632,652 | B1 | 10/2003 | Austin et al. |
| 6,714,287 | B2 | 3/2004 | Berndt |
| 6,723,290 | B1 | 4/2004 | Wardlaw |
| 6,844,201 | B2 | 1/2005 | Malmqvist et al. |
| 6,866,823 | B2 | 3/2005 | Wardlaw |
| 6,869,570 | B2 | 3/2005 | Wardlaw |
| 6,893,850 | B2 | 5/2005 | Ostuni et al. |
| 6,921,514 | B1 | 7/2005 | Vetter et al. |
| 6,929,953 | B1 | 8/2005 | Wardlaw |
| 6,939,032 | B2 | 9/2005 | Cosby et al. |
| 7,101,341 | B2 | 9/2006 | Tsukashima et al. |
| 7,179,423 | B2 | 2/2007 | Bohm et al. |
| 7,223,592 | B2 * | 5/2007 | Shea .................. B01J 19/0046 |
| | | | 435/287.2 |
| 7,282,367 | B2 | 10/2007 | Kawamura |
| 7,393,658 | B2 | 7/2008 | Carbonell et al. |
| 7,410,617 | B2 | 8/2008 | Sakamoto |
| 7,410,807 | B2 | 8/2008 | D'Aurora |
| 7,468,160 | B2 | 12/2008 | Thompson et al. |
| 7,510,841 | B2 | 3/2009 | Stuelpnagel et al. |
| 7,510,848 | B2 | 3/2009 | Hammond et al. |
| 7,547,424 | B2 | 6/2009 | Haab et al. |
| 7,731,901 | B2 | 6/2010 | Wardlaw |
| 7,738,094 | B2 | 6/2010 | Goldberg |
| 7,799,558 | B1 * | 9/2010 | Dultz .................. B01L 3/50853 |
| | | | 435/287.2 |
| 7,850,916 | B2 | 12/2010 | Wardlaw |
| 7,862,773 | B2 | 1/2011 | Ibrahim |
| 7,863,411 | B2 | 1/2011 | Hammond et al. |
| 7,897,376 | B2 | 3/2011 | Porter et al. |
| 7,901,897 | B2 | 3/2011 | Stuelpnagel et al. |
| 7,903,241 | B2 | 3/2011 | Wardlaw et al. |
| 7,929,121 | B2 | 4/2011 | Wardlaw et al. |
| 7,929,122 | B2 | 4/2011 | Wardlaw et al. |
| 7,943,093 | B2 | 5/2011 | Adrien et al. |
| 7,951,599 | B2 | 5/2011 | Levine et al. |
| 7,995,194 | B2 | 8/2011 | Wardlaw et al. |
| 8,045,165 | B2 | 10/2011 | Wardlaw et al. |
| 8,058,073 | B2 | 11/2011 | Chiapperi et al. |
| 8,077,296 | B2 | 12/2011 | Wardlaw et al. |
| 8,081,303 | B2 | 12/2011 | Levine et al. |
| 8,133,738 | B2 | 3/2012 | Levine et al. |
| 8,144,504 | B2 | 3/2012 | Kim et al. |
| 8,158,434 | B2 | 4/2012 | Wardlaw |
| 8,221,985 | B2 | 7/2012 | Wardlaw et al. |
| 8,241,572 | B2 | 8/2012 | Wardlaw |
| 8,269,954 | B2 | 9/2012 | Levine et al. |
| 8,284,384 | B2 | 10/2012 | Levine et al. |
| 8,287,820 | B2 | 10/2012 | Williams et al. |
| 8,310,658 | B2 | 11/2012 | Wardlaw et al. |
| 8,310,659 | B2 | 11/2012 | Wardlaw et al. |
| 8,319,954 | B2 | 11/2012 | Wardlaw et al. |
| 8,326,008 | B2 | 12/2012 | Lalpuria et al. |
| 8,338,579 | B2 | 12/2012 | Adams et al. |
| 8,361,799 | B2 | 1/2013 | Levine et al. |
| 8,367,012 | B2 | 2/2013 | Wardlaw |
| 8,462,332 | B2 | 6/2013 | Pugia et al. |
| 8,467,063 | B2 | 6/2013 | Wardlaw et al. |
| 8,472,693 | B2 | 6/2013 | Davis et al. |
| 8,481,282 | B2 | 7/2013 | Levine et al. |
| 8,502,963 | B2 | 8/2013 | Levine et al. |
| 8,513,032 | B2 | 8/2013 | Jablonski et al. |
| 8,569,076 | B2 | 10/2013 | Wardlaw et al. |
| 8,594,768 | B2 | 11/2013 | Phillips et al. |
| 8,604,161 | B2 | 12/2013 | Hammond et al. |
| 8,628,952 | B2 | 1/2014 | Stuelpnagel et al. |
| 8,633,013 | B2 * | 1/2014 | Kaiser .............. B01L 3/502715 |
| | | | 435/287.2 |

(56) References Cited

U.S. PATENT DOCUMENTS

| | | |
|---|---|---|
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,005,901 B2 | 4/2015 | Gayda et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 9,873,118 B2 * | 1/2018 | Verrant ................ B01L 3/5027 |
| 2001/0055882 A1 | 12/2001 | Ostuni |
| 2002/0126271 A1 | 9/2002 | Berndt |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0180685 A1 | 7/2008 | de Laga et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0191643 A1 * | 7/2009 | Boehm ............... B01L 3/50273 |
| | | 436/164 |
| 2009/0211344 A1 | 8/2009 | Wang |
| 2009/0215050 A1 * | 8/2009 | Jenison ................ C12Q 1/6844 |
| | | 435/6.1 |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298116 A1 * | 12/2009 | Fang .................... B81C 99/009 |
| | | 435/29 |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0189671 A1 * | 7/2013 | Hoh ....................... C12M 23/34 |
| | | 435/3 |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2015/0036131 A1 | 2/2015 | Salsman |
| 2015/0184235 A1 * | 7/2015 | Reda ................. B01L 3/502715 |
| | | 506/9 |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2016/0350914 A1 | 12/2016 | Champlin et al. |
| 2017/0021356 A1 | 1/2017 | Dority et al. |
| 2017/0038401 A1 | 2/2017 | Holmes et al. |
| 2017/0045504 A1 | 2/2017 | Blom et al. |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 2848196 | 3/2015 |
| EP | 3026433 | 6/2016 |
| EP | 1949310 B1 | 2/2019 |
| JP | 08334702 A | 12/1996 |
| JP | 2015121421 A | 7/2015 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |

(56) References Cited

FOREIGN PATENT DOCUMENTS

| WO | 2014183049 | 11/2014 |
| WO | 2014205576 | 12/2014 |
| WO | 2017027643 | 2/2017 |
| WO | 2017048871 | 3/2017 |
| WO | 2017048881 | 3/2017 |

OTHER PUBLICATIONS

Written Opinion for PCT/US2018/017713 established by ISA/KR, dated Jun. 20, 2018.

Sun, Wei et al., Rapid antimicrobial susceptibility test for identification of new therapeutics and drug combinations against multidrug-resistant bacteria, Emerg. Microbes Infect., Nov. 9, 2016.

Jahanmehr, S A H et al., Simple technique for fluorescence staining of blood cells with acridine orange, Technical Methods, Feb. 12, 1987.

Van Vliet, Dillys et al., Prediction of asthma exacerbations in children by innovative exhaled inflammatory markers: Results of a longitudinal study, Plos One, Mar. 23, 2015, vol. 10. No. 3, e0119434.

\* cited by examiner

A

B

C

A

B

ASSAY USING DIFFERENT SPACING HEIGHTS

CROSS REFERENCE

This application is a 371 national stage application of International Application PCT/US2018/017713, filed Feb. 9, 2018, which claims the benefit of priority to U.S. provisional application No. 62/457,133, filed on Feb. 9, 2017, U.S. provisional application No. 62/539,718, filed on Aug. 1, 2017, and U.S. provisional application 62/577,370, filed on Oct. 26, 2017, each are incorporated by reference in their entirety for all purposes.

FIELD

Among other things, the present invention is related to devices and methods of performing biological and chemical assays.

BACKGROUND

In biological and chemical assays, it has a need for new ways to manipulate a sample. The present invention, among other things, provides the devices and methods in manipulate a sample for the purpose of assaying.

SUMMARY

The following brief summary is not intended to include all features and aspects of the present invention.

One aspect of the present invention is to provide a device that make a sample sandwiched between two plates to have different thickness in different areas of the plates.

Another aspect of the present invention is to control the spacing (i.e. gap) between two plate to selectively lyse only certain types of cells but not other cell types.

Another aspect of the present invention is to control the spacing (i.e. gap) between two plate using spacers, and to control the spacing (hence the sample thickness) precisely in sub-micron precision and uniformly over a large area.

Another aspect of the present invention is to use the spacers to make a sample sandwiched between two plates to have different thickness in different areas of the plates.

And another aspect of the present invention is to use different sample thickness in different areas of the plates which sandwiched the sample between to perform certain assay functions, that include, but not limited to, (i) selectively lysing cells in different areas, (ii) different number of analytes in a sample in different area, (iii) reducing Hook effects, and others.

BRIEF DESCRIPTION OF FIGURES

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other meaning.

A. QMAX DEVICE WITH DIFFERENT LEVEL HEIGHTS (061)

Figure 1:
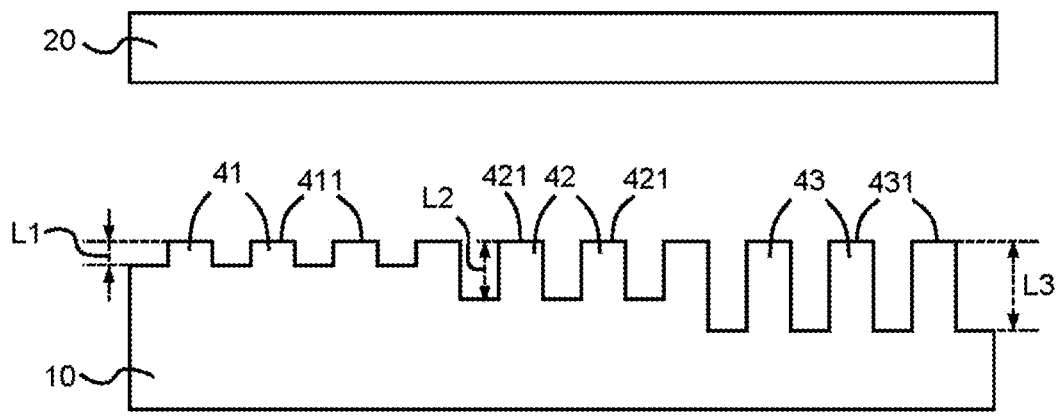
FIG. 1 shows schematics of an exemplary embodiment of a QMAX device, which comprises spacers of different level heights.
Figure 1:
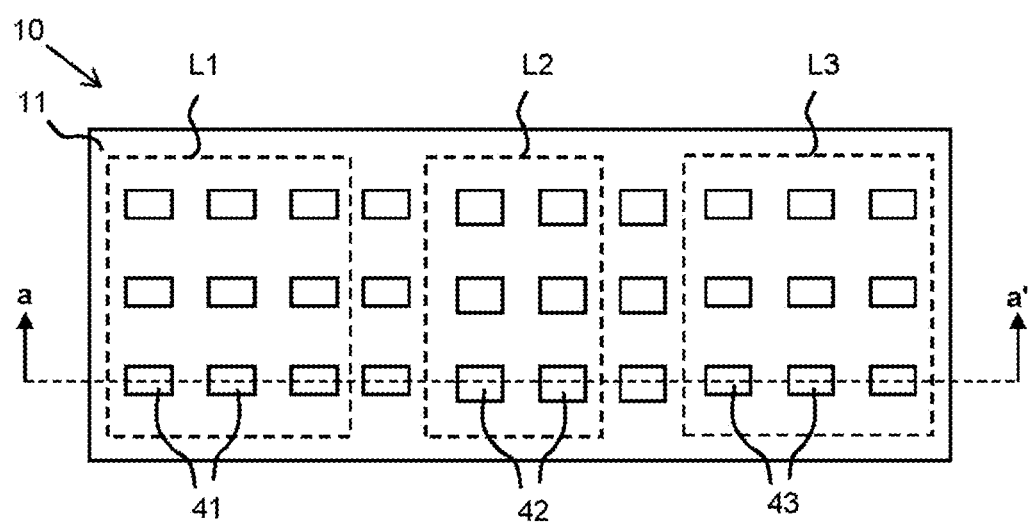
Figure 2:
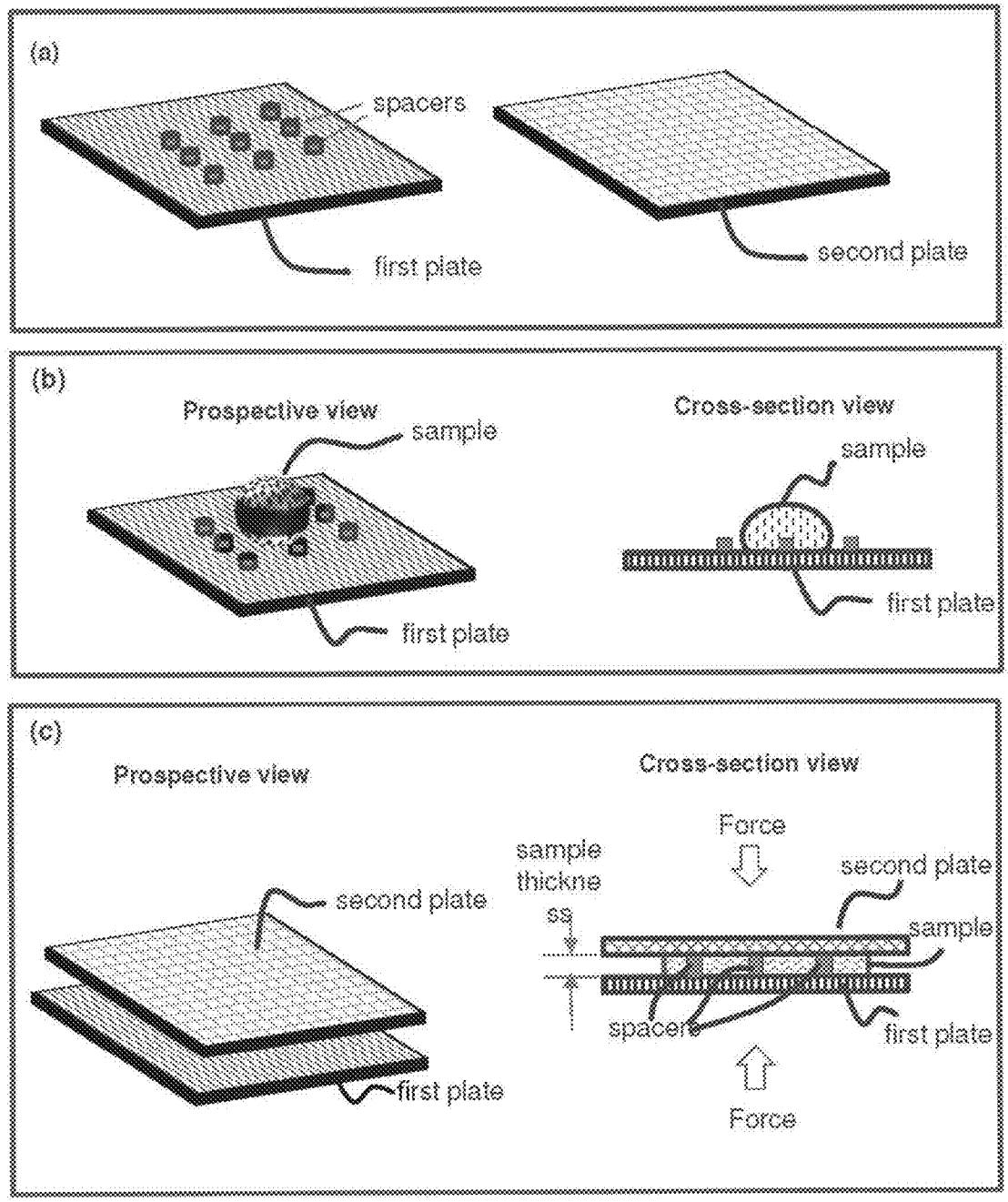
FIG. 2 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).

FIG. 1 shows schematics of an exemplary embodiment of a QMAX device, which comprises a first plate 10, a second plate 20, and a plurality of spacers (41, 42, 43) fixed on the inner surface of the first plate 11 (not indicated in cross-sectional view). Panel (A) shows a cross-sectional view of the device, while panel (B) shows a top view of the first plate 10 and the spacers (41, 42, and 43). However, it should be noted that, in some embodiments, the spacers are fixed on the second plate 20, or both the first and second plates. As shown in panel (A), the first plate 10 has different thickness at different locations. Each spacer has a top end and a height that is the vertical distance measured from the top end to the closest point on the inner surface adjacent to the spacer. As shown in the figure, there are three different sets of spacers 41, 42, and 43. Each set of spacers have the same height, i.e. spacers 41 have a height L1, spacers 42 have a height L2, and spacers 42 have a height L3. Different sets of spacers differ from one another at least in their heights, i.e., L1, L2, and L3 are different from one another. On the other hand, the top end of each spacer (411, 421, and 431 as indicated in the cross-sectional view) are substantially aligned on the same plane, as indicated by the dashed line in panel (A). Structurally the spacers in different sets seem to "stem from" different levels of the first plate inner surface. Therefore, the height of the spacers is also termed as "level height" in this context. As such, the QMAX device as shown in FIG. 1 is said to have different level heights. However, it should be noted that, in some embodiments, there are more than one set of spacers having different level heights. In some embodiments, there are 2 sets or more, 3 sets or more, 4 sets or more, 5 sets or more, 6 sets or more, 7 sets or more, 8 sets or more, 9 sets or more, 10 sets or more, 15 sets or more, 20 sets or more, 30 sets or more, 50 sets or more of spacers having different level heights.

Examples of Present Invention

A1. A device for analyzing a liquid sample, comprising:
 a first plate, a second plate, and spacers, wherein:
 i. the plates are movable relative to each other into different configurations;
 ii. one or both plates are flexible;
 iii. the first plate has, on its inner surface, a first and a second sample contact areas at different locations, and the first plate has a first and second thickness at the first and second sample contact areas, respectively, wherein the sample contact areas are for contacting a sample suspected of containing a target analyte, and wherein the first thickness is different from the second thickness;
 iv. the spacers are fixed to the first plate inner surface, and have a predetermined substantially uniform height in each sample contact area; and
 v. each of the spacers has a top end, and the top ends of the spacers are substantially aligned in one surface;
 wherein one of the configurations is an open configuration, in which: the two plates are partially or entirely separated apart, the spacing between the plates is not regulated by the spacers, and the sample is deposited on one or both of the plates; and
 wherein another of the configurations is a closed configuration, which is configured after the sample deposition in the open configuration, and in the closed configuration: at least part of the deposited sample is compressed by the two plates into a layer that is confined by the two plates and has a respective substantially uniform thickness over each of the sample contact areas, wherein the uniform thickness of the layer is confined by the respective sample contact area and is regulated by the plates and the spacers in the respective sample contact area.

A2. The device of paragraph A1, wherein the uniform heights of the spacers are in the range of 0.5 to 100 μm.

A3. The device of any one of prior paragraphs, wherein the uniform heights of the spacers are in the range of 0.5 to 20 μm.

A4. The device of any one of prior paragraphs, wherein the difference between the uniform heights of the spacers in the first and second sample contact areas is in the range of 0.5 to 100 □m.

A5. The device of any one of prior paragraphs, wherein the difference between the uniform heights of the spacers in the first and second sample contact areas is in the range of 0.5 to 50 □m.

A6. The device of any one of prior paragraphs, wherein the spacers have a predetermined substantially constant inter-spacer distance in each sample contact area;

A7. The device of paragraph A6, wherein the constant inter-spacer distances of the spacers are in the range of 7 to 200 □m.

A8. The device of paragraph A6, wherein the constant inter-spacer distances of the spacers are in the range of 50 to 150 □m.

A9. The device of any one of prior paragraphs, wherein a separation between edges of neighboring sample contact areas is in the range of 20 □m to 1 mm.

A10. The device of any one of prior paragraphs, wherein a separation between edges of neighboring sample contact areas is in the range of 100 to 500 □m.

A11. The device of any one of prior paragraphs, wherein an average value of the uniform thickness of the layer in each sample contact area is substantially the same as the uniform height of the spacers therein with a variation of less than 10%.

A12. The device of any one of prior paragraphs, wherein the first plate has, on at least one of the sample contact areas, a binding site that has a predetermined lateral area and contains a capture agent capable of binding and immobilizing the target analyte.

A13. The device of paragraph A12, wherein in the closed configuration, the uniform thickness of the layer in any one of the sample contact areas is substantially less than the predetermined lateral area of the binding site therein.

A14. The device of any one of prior paragraphs, wherein the second plate has a first and a second sample contact areas at different locations that are corresponding to the first and the second sample contact areas of the first plate, respectively, wherein the respectively corresponding sample contact areas are over one another in the closed configuration.

A15. The device of paragraph A14, wherein the second plate has, on at least one of the sample contact areas, a storage site that has a predetermined lateral area and contains a detection agent, that upon contacting the sample, dissolves and diffuses in the sample.

A16. The device of any one of prior paragraphs, wherein a smallest separation between edges of neighboring sample contact areas is substantially larger than the distance that a target analyte or detection agent can diffuse in a relevant time, wherein the relevant time is:
  i. about equal to or longer than the time that it takes for the target analyte to diffuse across the thickness of the uniform thickness layer at the closed configuration; and
  ii. shorter than the time that it takes for the target analyte to laterally diffuse across the linear dimension of the predetermined area of the binding site.

A17. The device of any one of prior paragraphs, wherein there is no fluidic isolation between neighboring sample contact areas.

C1. A method for analyzing a liquid sample, comprising the steps of:
  (a) obtaining a sample suspected of containing a target analyte;
  (b) obtaining a first plate, a second plate, and spacers, wherein:
    i. the plates are movable relative to each other into different configurations;
    ii. one or both plates are flexible;
    iii. the first plate has, on its inner surface, a first and a second sample contact areas at different locations, and the first plate has a first and second thickness at the first and second sample contact areas, respectively, wherein the sample contact areas are for contacting a sample suspected of containing a target analyte, and wherein the first thickness is different from the second thickness;
    iv. the spacers are fixed to the first plate inner surface, and have a predetermined substantially uniform height in each sample contact area; and
    v. each of the spacers has a top end, and the top ends of the spacers are substantially aligned in one surface;
  (c) depositing the sample on one or both of the plates when the plates are in the open configuration,
    wherein the open configuration is a configuration in which the two plates are partially or entirely separated apart, the spacing between the two plates is not regulated by the spacers, and the sample is deposited on one or both of the plates;
  (d) after (c), bringing the two plates together and pressing the plates into the closed configuration,
    wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and
    wherein the closed configuration is configured after the sample deposition in the open configuration, and in the closed configuration: at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area; and
  (e) analyzing the target analyte in the layer of uniform thickness when the plates are in the closed configuration.

C2. The method of any one of paragraph C1 or CC1, wherein the uniform heights of the spacers are in the range of 0.5 to 100 μm.

C3. The method of any one of prior method paragraphs, wherein the uniform heights of the spacers are in the range of 0.5 to 20 μm.

C4. The method of any one of prior method paragraphs, wherein the difference between the uniform heights of the spacers in the different sample contact areas is in the range of 0.5 to 100 □m.

C5. The method of any one of prior method paragraphs, wherein the difference between the uniform heights of the spacers in the different sample contact areas is in the range of 0.5 to 50 □m.

C6. The method of any one of prior method paragraphs, wherein the spacers have a predetermined substantially constant inter-spacer distance in each sample contact area;

C7. The method of paragraph C6, wherein the constant inter-spacer distances of the spacers are in the range of 7 to 200 □m.

C8. The method of paragraph C6, wherein the constant inter-spacer distances of the spacers are in the range of 50 to 150 □m.

C9. The method of any one of prior method paragraphs, wherein a separation between edges of neighboring sample contact areas is in the range of 20 □m to 1 mm.

C10. The method of any one of prior method paragraphs, wherein a separation between edges of neighboring sample contact areas is in the range of 100 to 500 □m.

C11. The method of any one of prior method paragraphs, wherein an average value of the uniform thickness of the layer in each sample contact area is substantially the same as the uniform height of the spacers therein with a variation of less than 10%.

C12. The method of any one of prior method paragraphs, further comprising: after step (d) and before step (e), removing the conformable pressing force, wherein the thickness of the layer of uniform thickness after removal of the conformable pressing force: (i) is substantially the same as of the layer of uniform thickness before removing the conformable pressing force and (ii) deviates from the spacer height by less than 10%.

C13. The method of any one of prior method paragraphs, wherein the conformable pressing is performed by human hand.

C14. The method of any one or prior method paragraphs, wherein the conformable pressing is provided by a pressured liquid, a pressured gas, or a conformable material.

C15. The method of any one of prior method paragraphs, wherein the sample deposition of step (c) is a deposition directly from a subject to the plate without using any transferring devices.

C16. The method of any one of prior method paragraphs, wherein during the deposition of step (c), the amount of the sample deposited on the plate is unknown.

C17. The method of any one or prior method paragraphs, wherein the analyzing in step (e) comprises performing an assay in the layer of uniform thickness.

C18. The method of paragraph C17, wherein the assay is a binding assay or biochemistry assay.

C19. The method of any one of prior method paragraphs, wherein the first plate has, on at least one of the sample contact areas, a binding site that has a predetermined lateral area and contains a capture agent capable of binding and immobilizing the target analyte.
C20. The method of paragraph C19, wherein in the closed configuration, the uniform thickness of the layer in any one of the sample contact areas is substantially less than the predetermined lateral area of the binding site therein.
C21. The method of any one of prior method paragraphs, wherein the second plate has, on at least one of the sample contact areas, a storage site that has a predetermined lateral area and contains a detection agent of a concentration, that upon contacting the sample, dissolves into the sample and diffuses in the sample.
C22. The method of any one of prior method paragraphs, wherein a smallest separation between the edges of neighboring sample contact areas is substantially larger than the distance that a target analyte or detection agent can diffuse in a relevant time, wherein there is no fluidic isolation between the neighboring sample contact areas, wherein the relevant time length is:
  i. about equal to or longer than the time that it takes for the target analyte to diffuse across the thickness of the uniform thickness layer at the closed configuration; and
  ii. shorter than the time that it takes the target analyte to laterally diffuse across the linear dimension of the predetermined area of the binding site.
C23. The method of any one of prior method paragraphs, wherein the analyzing of step (e) comprises:
  (1) incubating the sample for a relevant time length and then stopping the incubation; or
  (2) incubating the sample for a time that is equal or longer than the minimum of a relevant time length, and then assessing, within a time period that is equal to or less than the maximum of the relevant length of time, the binding of each target analyte to a binding site,
  thereby producing a reaction in which, at the end of the incubation in (1) or during the assessing in (2), the majority of the target analyte in the capture agent-target analyte-detection agent sandwich bound to each binding site is from a corresponding relevant volume of the sample;
  wherein the incubation allows each target analyte to bind to a binding site and a detection agent, wherein the corresponding relevant volume is a portion of the sample that is above the corresponding storage site at the closed configuration.
C24. The method of any one of prior method paragraphs, wherein the reaction is saturated in less than 60 seconds.
C25. The method of any one or prior method paragraphs, wherein the relevant time length is in the range of 60 seconds to 30 minutes.
C26. The method of any one of prior method paragraphs, wherein the analyzing in step (e) comprises measuring a target analyte-related signal selected from the group consisting of:
  i. luminescence selected from photoluminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; and
  vi. any combination of i-v,
  wherein the target analyte-related signal is a signal that is proportional to and reflects the amount of the target analyte in the sample.
C27. The method of paragraph C26, wherein the analyzing step (e) comprises:
  determining an optimal signal from the target analyte-related signals measured from relevant sample contact areas, wherein the relevant sample contact areas are the sample contact areas that contain the binding site and/or storage site for detecting the same target analyte.
C28. The method of paragraph C26, wherein the optimal target analyte-related signal is determined by selecting the measured target analyte-related signal within a range between minimum and maximum detection thresholds, wherein the minimum and maximum detection thresholds of the plates and a detector used for the signal measuring.
C29. The method of paragraph C26, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.
C30. The method of any one of prior method paragraphs, wherein the analyzing step (e) comprises calculating the volume of a relevant sample volume by measuring the lateral area of the relevant sample volume and calculating the volume from the lateral area and the predetermined spacer height, wherein the relevant volume is a part of or an entire volume of the sample.
C31. The method of any one of prior method paragraphs, wherein the analyzing step (e) comprises reading, image analysis, or counting of the target analyte, or a combination of thereof.
C32. The method of any one of prior method paragraphs, further comprising one or more washes.
C33. The method of any one of prior method paragraphs, wherein the deposited sample has a total volume less 0.5 □L.
C34. The method of any one of prior method paragraphs, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.
C35. The method of any one of prior method paragraphs, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.
C36. The method of any one of prior method paragraphs, wherein the sample is an environmental gaseous sample from a source selected from the group consisting of: the air, underwater heat vents, industrial exhaust, vehicular exhaust, and any combination thereof.
C37. The method of any one of prior method paragraphs, wherein the sample is a foodstuff sample selected from the group consisting of: raw ingredients, cooked food, plant and animal sources of food, preprocessed food, and partially or fully processed food, and any combination thereof.

C38. The method of any one of prior method paragraphs, wherein the sample is human blood, and the depositing step comprises: (a) pricking the skin of a human release a droplet of blood onto the skin; and (b) contacting the droplet of blood with the filter without use of a blood transfer tool.

D1. A method for a parallel multiplexed assay of a liquid sample, comprising the steps of:
  (a) obtaining a sample suspected of containing a target analyte
  (b) obtaining a first plate, a second plate, and spacers, wherein:
    i. the plates are movable relative to each other into different configurations, including an open configuration and a closed configuration;
    ii. one or both of the plates are flexible;
    iii. the first plate has, on its inner surface, a first and a second sample contact areas at different locations, and the first plate has a first and second thickness at the first and second sample contact areas, respectively, wherein the sample contact areas are for contacting a sample suspected of containing a target analyte, and wherein the first thickness is different from the second thickness;
    iv. the first plate has, on at least one of the sample contact areas, a binding site that has a predetermined lateral area and contains a capture agent capable of binding and immobilizing the target analyte;
    v. the second plate has, on at least one of the sample contact areas, a storage site that has a predetermined lateral area and contains a detection agent, that upon contacting the sample, dissolves and diffuses in the sample;
    vi. the spacers are fixed to the respective inner surface of one or both of the plates and have a predetermined substantially uniform height in each sample contact area; and
    vii. each of the spacers has a top end, and the top ends of the spacers are substantially aligned in one surface;
    wherein each capture agent, target analyte and corresponding detection agent are capable of forming a capture agent-target analyte-detection agent sandwich in a binding site of the first plate;
  (c) depositing the sample on one or both of the plates when the plates are in the open configuration,
    wherein the open configuration is a configuration in which the two plates are partially or entirely separated apart, the spacing between the plates is not regulated by the spacers, and the sample is deposited on one or both of the plates;
  (d) after (c), bringing the two plates together and pressing the plates into the closed configuration,
    wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and
    wherein the closed configuration is configured after the sample deposition at the open configuration, and in the closed configuration: the corresponding sample contact areas on the two plates are over one another, respectively; and at least part of the deposited sample is compressed by the two plates into a layer that is confined by the two plates and has a respective substantial uniform thickness over each of the sample contact areas, wherein the uniform thickness of the layer is confined by the respective sample contact area of the plates and is regulated by the plates and the spacers in the respective sample contact area; and
  (e) after (d) and while the plates are in the closed configuration:
    (1) incubating the sample for a relevant time length and then stopping the incubation; or
    (2) incubating the sample for a time that is equal or longer than the minimum of a relevant time length, and then assessing, within a time period that is equal to or less than the maximum of the relevant length of time, the binding of each target analyte to a binding site,
  thereby producing a reaction in which, at the end of the incubation in (1) or during the assessing in (2), the majority of the target analyte in the capture agent-target analyte-detection agent sandwich bound to each binding site is from a corresponding relevant volume of the sample;
  wherein the incubation allows each target analyte to bind to a binding site and a detection agent, wherein the corresponding relevant volume is a portion of the sample that is above the corresponding storage site at the closed configuration, and
  wherein the relevant time is:
    (i) about equal to or longer than the time that it takes for the target analyte to diffuse across the thickness of the uniform thickness layer at the closed configuration; and
    (ii) shorter than the time that it takes for the target analyte to laterally diffuse across the linear dimension of the predetermined area of the binding site.

D2. The method of paragraph D1, wherein step (e) comprises measuring a target analyte-related signal selected from the group consisting of:
  i. luminescence selected from photoluminescence, electroluminescence, and electrochemiluminescence;
  ii. light absorption, reflection, transmission, diffraction, scattering, or diffusion;
  iii. surface Raman scattering;
  iv. electrical impedance selected from resistance, capacitance, and inductance;
  v. magnetic relaxivity; and
  vi. any combination of i-v,
  wherein the target analyte-related signal is a signal that is proportional to and reflects the binding of target analyte to the binding site.

D3. The method of paragraph D2, wherein the analyzing step (e) comprises:
  determining an optimal signal from the target analyte-related signals measured from relevant sample contact areas, wherein the relevant sample contact areas are the sample contact areas that contain the binding site and/or storage site for detecting the same target analyte.

D4. The method of paragraph D3, wherein the optimal target analyte-related signal is determined by selecting the measured target analyte-related signal within a range between minimum and maximum detection thresholds, wherein the minimum and maximum detection thresholds of the plates and a detector used for the signal measuring.

D5. The method of paragraph D3, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

E1. The device or method of any one of prior paragraphs, wherein the binding site is defined by a patch of dried reagent.

E2. The device or method of any one of prior paragraphs, wherein the binding site is between a pair of electrodes.

E3. The device or method of any one of prior paragraphs, wherein one or both plate inner surfaces comprise one or a plurality of amplification sites that are each capable of amplifying the target analyte-related signal when the target analyte is within 500 nm from an amplification site.

E4. The device or method of any one of prior paragraphs, wherein the plates have a thickness of less than 200 µm.

E5. The device or method of any one of prior paragraphs, wherein the plates have a thickness of less than 100 µm.

E6. The device or method of any one of prior paragraphs, wherein each of the plates has an area of less than 5 cm$^2$.

E7. The device or method of any one of prior paragraphs, wherein each of the plates has an area of less than 2 cm$^2$.

E8. The device or method of any one of prior paragraphs, wherein at least one of the plates is partially or entirely transparent.

E9. The device or method of any one of prior paragraphs, wherein at least one of the plates is made from a flexible polymer.

E10. The device or method of any one of prior paragraphs, wherein at least one of the plates is a flexible plate, and the thickness of the flexible plate times the Young's modulus of the flexible plate is in the range of 60 to 75 GPa-µm.

E11. The device or method of any one of prior paragraphs, wherein the spacers are spacers with a cross sectional shape selected from round, polygonal, circular, square, rectangular, oval, elliptical, or any combination of the same.

E12. The device or method of any one of prior paragraphs, wherein the spacers have a pillar shape and a substantially flat top surface, wherein, for each spacer, the ratio of the lateral dimension of the spacer to its height is at least 1.

E13. The device or method of any one of prior paragraphs, wherein each spacer has the ratio of the lateral dimension of the spacer to its height is at least 1.

E14. The device or method of any one of prior paragraphs, wherein the minimum lateral dimension of spacer is less than or substantially equal to the minimum dimension of a target analyte in the sample.

E15. The device or method of any one of prior paragraphs, wherein the spacers have a pillar shape, and the sidewall corners of the spacers have a round shape with a radius of curvature at least 1 µm.

E16. The device or method of any one of prior paragraphs, wherein the spacers have a density of at least 100/mm$^2$.

E17. The device or method of any one of prior paragraphs, wherein the spacers have a density of at least 1000/mm$^2$.

E18. The device or method of any one of prior paragraphs, wherein the spacers have a filling factor of at least 1%, wherein the filling factor is the ratio of the spacer area in contact with the layer of uniform thickness to the total plate area in contact with the layer of uniform thickness.

E19. The device or method of any one of prior paragraphs, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

E20. The device or method of any one of prior paragraphs, wherein
a. at least one of the plates is flexible, and
b. for the flexible plate, the fourth power of the inter-spacer-distance (ISD) divided by the thickness of the flexible plate (h) and the Young's modulus (E) of the flexible plate, $ISD^4/(hE)$, is equal to or less than 106 um$^3$/GPa.

E21. The device or method of any one of prior paragraphs, wherein the spacers are fixed on a plate by directly embossing the plate or injection molding of the plate.

E22. The device or method of any one of prior paragraphs, wherein the materials of the plate and the spacers are independently selected from polystyrene, PMMG, PC, COC, COP, or another plastic.

Device and Assay with High Uniformity

Sample Viscosity

In the present invention, the samples to be manipulated and/or analyzed can have a various range of viscosities. For examples, the typical viscosity range is 1.31 to 0.28 (mPa s) from 10 to 100° C. for water; 1.05 to 0.70 (mPa s) from 19 to 37° C. for PBS buffer; 2.4 to 1.45 (mPa s) from 17 to 45° C. for plasma; 2.87 to 2.35 (mPa s) from 35 to 42° C. for whole blood; and 0.797 to 0.227 (mPa s) from 0 to 100° C. for methanol. In some embodiments, the sample has a viscosity from 0.1 to 4 (mPa s). In some embodiments, the sample has viscosity of from 4 to 50 (mPa s). In a preferred embodiment, the sample has viscosity of from 0.5 to 3.5 (mPa s).

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

IDS^4/hE

AA1. A device for forming a thin fluidic sample layer with a uniform predetermined thickness by pressing, comprising:
 a first plate, a second plate, and spacers, wherein:
  i. the plates are movable relative to each other into different configurations;
  ii. one or both plates are flexible;
  iii. each of the plates comprises an inner surface that has a sample contact area for contacting a fluidic sample;
  iv. each of the plates comprises, on its respective outer surface, a force area for applying an pressing force that forces the plates together;
  v. one or both of the plates comprise the spacers that are permanently fixed on the inner surface of a respective plate;
  vi. the spacers have a predetermined substantially uniform height that is equal to or less than 200 microns, and a predetermined fixed inter-spacer-distance;
  vii. the fourth power of the inter-spacer-distance (ISD) divided by the thickness (h) and the Young's modulus (E) of the flexible plate ($ISD^4/(hE)$) is $5 \times 10^6$ um$^3$/GPa or less; and
  viii. at least one of the spacers is inside the sample contact area;
 wherein one of the configurations is an open configuration, in which: the two plates are partially or completely separated apart, the spacing between the plates is not regulated by the spacers, and the sample is deposited on one or both of the plates;
 wherein another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A method of forming a thin fluidic sample layer with a uniform predetermined thickness by pressing, comprising the steps of:
 (a) obtaining a device of embodiment AA1;
 (b) depositing a fluidic sample on one or both of the plates; when the plates are configured in an open configuration, wherein the open configuration is a configuration in which the two plates are partially or completely separated apart and the spacing between the plates is not regulated by the spacers;
 (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA3. A device for analyzing a fluidic sample, comprising:
 a first plate, a second plate, and spacers, wherein:
  i. the plates are movable relative to each other into different configurations;
  ii. one or both plates are flexible;
  iii. each of the plates has, on its respective inner surface, a sample contact area for contacting a fluidic sample,
  iv. one or both of the plates comprise the spacers and the spacers are fixed on the inner surface of a respective plate;
  v. the spacers have a predetermined substantially uniform height that is equal to or less than 200 microns, and the inter-spacer-distance is predetermined;
  vi. the Young's modulus of the spacers multiplied by the filling factor of the spacers is at least 2 MPa; and
  vii. at least one of the spacers is inside the sample contact area; and
 wherein one of the configurations is an open configuration, in which: the two plates are partially or completely separated apart, the spacing between the plates is not regulated by the spacers, and the sample is deposited on one or both of the plates; and
 wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA4. A method of forming a thin fluidic sample layer with a uniform predetermined thickness by pressing, comprising the steps of:
 (a) obtaining a device of embodiment AA3;
 (b) depositing a fluidic sample on one or both of the plates; when the plates are configured in an open configuration, wherein the open configuration is a configuration in which the two plates are partially or completely separated apart and the spacing between the plates is not regulated by the spacers;
 (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA5. A device for analyzing a fluidic sample, comprising:
a first plate and a second plate, wherein:
i. the plates are movable relative to each other into different configurations;
ii. one or both plates are flexible;
iii. each of the plates has, on its respective surface, a sample contact area for contacting a sample that contains an analyte,
iv. one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area;

wherein one of the configurations is an open configuration, in which: the two plates are separated apart, the spacing between the plates is not regulated by the spacers, and the sample is deposited on one or both of the plates; and wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA6. A method of forming a thin fluidic sample layer with a uniform predetermined thickness by pressing, comprising the steps of:
(a) obtaining a device of embodiment AA5;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA7. A device for forming a thin fluidic sample layer with a uniform predetermined thickness by pressing, comprising:
a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined fixed inter-spacer-distance;
vii. a ratio of the inter-spacer-distance to the spacer width is 1.5 or larger; and
viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA8. A method of forming a thin fluidic sample layer with a uniform predetermined thickness by pressing with an imprecise pressing force, comprising the steps of:
(a) obtaining a device of embodiment AA7;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

The devices or methods of any prior embodiment, wherein the spacers have a shape of pillar with a foot fixed on one of the plate and a flat top surface for contacting the other plate.

The devices or methods of any prior embodiment, wherein the spacers have a shape of pillar with a foot fixed on one of the plate, a flat top surface for contacting the other plate, substantially uniform cross-section.

The devices or methods of any prior embodiment, wherein the spacers have a shape of pillar with a foot fixed on one of the plate and a flat top surface for contacting the other plate, wherein the flat top surface of the pillars has a variation in less than 10 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 10 nm, 20 nm, 30 nm, 100 nm, 200 nm, or in a range of any two of the values.

The devices or methods of any prior embodiment, wherein the Young's modulus of the spacers multiplied by the filling factor of the spacers is at least 2 MPa.

The devices or methods of any prior embodiment, wherein the sample comprises an analyte and the predetermined constant inter-spacer distance is at least about 2 times larger than the size of the analyte, up to 200 um.

The devices or methods of any prior embodiment, wherein the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

The devices or methods of any prior embodiment, wherein a fourth power of the inter-spacer-distance (IDS) divided by the thickness (h) and the Young's modulus (E) of the flexible plate (ISD$^4$/(hE)) is $5\times10^6$ um$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is $1\times10^6$ um$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is $5\times10^5$ um$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is $1\times10^5$ um$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is $1\times10^4$ um$^3$/GPa or less.

The devices or methods of any prior embodiment, wherein the Young's modulus of the spacers multiplied by the filling factor of the spacers is at least 20 MPa.

The devices or methods of any prior embodiment, wherein the ratio of the inter-spacing distance of the spacers to the average width of the spacer is 2 or larger.

The devices or methods of any prior embodiment, wherein the ratio of the inter-spacing distance of the spacers to the average width of the spacer is 2 or larger, and the Young's modulus of the spacers multiplied by the filling factor of the spacers is at least 2 MPa.

The devices or methods of any prior embodiment, wherein inter-spacer distance that is at least about 2 times larger than the size of the analyte, up to 200 um.

The devices or methods of any prior embodiment, wherein a ratio of the inter-spacer-distance to the spacer width is 1.5 or larger.

The devices or methods of any prior embodiment, wherein a ratio of the width to the height of the spacer is 1 or larger.

The devices or methods of any prior embodiment, wherein a ratio of the width to the height of the spacer is 1.5 or larger.

The devices or methods of any prior embodiment, wherein a ratio of the width to the height of the spacer is 2 or larger.

The devices or methods of any prior embodiment, wherein a ratio of the width to the height of the spacer is larger than 2, 3, 5, 10, 20, 30, 50, or in a range of any two the value.

The methods of any prior embodiment, wherein the force that presses the two plates into the closed configuration is an imprecise pressing force.

The methods of any prior embodiment, wherein the force that presses the two plates into the closed configuration is an imprecise pressing force provided by human hand.

The methods of any prior embodiment, wherein the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 20% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less.

The methods of any prior embodiment, wherein the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

The devices or methods of any prior embodiment, wherein the flexible plate has a thickness of in the range of 10 um to 200 um.

The devices or methods of any prior embodiment, wherein the flexible plate has a thickness of in the range of 20 um to 100 um.

The devices or methods of any prior embodiment, wherein the flexible plate has a thickness of in the range of 25 um to 180 um.

The devices or methods of any prior embodiment, wherein the flexible plate has a thickness of in the range of 200 um to 260 um.

The devices or methods of any prior embodiment, wherein the flexible plate has a thickness of equal to or less than 250 um, 225 um, 200 um, 175 um, 150 um, 125 um, 100 um, 75 um, 50 um, 25 um, 10 um, 5 um, 1 um, or in a range between the two of the values.

The devices or methods of any prior method, wherein the sample has a viscosity in the range of 0.1 to 4 (mPa s).

The devices or methods of any prior embodiment, wherein the flexible plate has a thickness of in the range of 200 um to 260 um.

The devices or methods of any prior embodiment, wherein the flexible plate has a thickness in the range of 20 um to 200 um and Young's modulus in the range 0.1 to 5 GPa.

1. The method of any prior claim, wherein the sample deposition of step (b) is a deposition directly from a subject to the plate without using any transferring devices.
2. The method any prior claim, wherein during the deposition of step (b), the amount of the sample deposited on the plate is unknown.
3. The method of any prior claim, wherein the method further comprises a analyzing step (e) that analyze the sample.
4. The method of any prior claim, wherein the analyzing step (e) comprises calculating the volume of a relevant sample volume by measuring the lateral area of the relevant sample volume and calculating the volume from the lateral area and the predetermined spacer height.
5. The method of any prior claim, wherein the analyzing step (e) comprises measuring:
   i. imaging, iiluminescence selected from photoluminescence, electroluminescence, and electrochemiluminescence,
   iii. surface Raman scattering,
   iv. electrical impedance selected from resistance, capacitance, and inductance,
   or
   v. any combination of i-iv.
6. The method of any prior claim, wherein the analyzing step (e) comprises reading, image analysis, or counting of the analyte, or a combination of thereof.
7. The method of any prior claim, wherein the sample contains one or plurality of analytes, and one or both plate sample contact surfaces comprise one or a plurality of binding sites that each binds and immobilize a respective analyte.
8. The method of any prior claim, wherein one or both plate sample contact surfaces comprise one or a plurality of storage sites that each stores a reagent or reagents, wherein the reagent(s) dissolve and diffuse in the sample during or after step (c).
9. The method of any prior claim, wherein one or both plate sample contact surfaces comprises one or a plurality of amplification sites that are each capable of amplifying a signal from the analyte or a label of the analyte when the analyte or label is within 500 nm from an amplification site.
10. The method of any prior claim, wherein:
    i. one or both plate sample contact surfaces comprise one or a plurality of binding sites that each binds and immobilize a respective analyte; or
    ii. one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or
    iii. one or a plurality of amplification sites that are each capable of amplifying a signal from the analyte or a label of the analyte when the analyte or label is 500 nm from the amplification site; or
    iv. any combination of i to iii.
11. The devices or methods of any prior embodiment, wherein the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
12. The devices or methods of any prior embodiment, wherein the layer of uniform thickness in the closed configuration is less than 150 um.
13. The method of any prior claim, wherein the pressing is provided by a pressured liquid, a pressed gas, or a conformal material.
14. The method of any prior claim, wherein the analyzing comprises counting cells in the layer of uniform thickness.
15. The method of any prior claim, wherein the analyzing comprises performing an assay in the layer of uniform thickness.
16. The devices or methods of any prior embodiment, wherein the assay is a binding assay or biochemical assay.
17. The method of any prior claim, wherein the sample deposited has a total volume less 0.5 uL
18. The method of any prior claim, wherein multiple drops of sample are deposited onto one or both of the plates.
19. The devices or methods of any prior embodiment, wherein the inter-spacer distance is in the range of 1 $\square$m to 120 $\sqsubset$m.
20. The devices or methods of any prior embodiment, wherein the inter-spacer distance is in the range of 120 $\square$m to 50 $\square$m.
21. The devices or methods of any prior embodiment, wherein the inter-spacer distance is in the range of 120 $\square$m to 200 $\sqsubset$m.
22. The device of any prior device claim, wherein the flexible plates have a thickness in the range of 20 um to 250 um and Young's modulus in the range 0.1 to 5 GPa.
23. The device of any prior device claim, wherein for a flexible plate, the thickness of the flexible plate times the Young's modulus of the flexible plate is in the range 60 to 750 GPa-um.
24. The device of any prior device claim, wherein the layer of uniform thickness sample is uniform over a lateral area that is at least 1 $mm^2$.
25. The device of any prior device claim, wherein the layer of uniform thickness sample is uniform over a lateral area that is at least 3 $mm^2$.
26. The device of any prior device claim, wherein the layer of uniform thickness sample is uniform over a lateral area that is at least 5 $mm^2$.
27. The device of any prior device claim, wherein the layer of uniform thickness sample is uniform over a lateral area that is at least 10 $mm^2$.
28. The device of any prior device claim, wherein the layer of uniform thickness sample is uniform over a lateral area that is at least 20 $mm^2$.
29. The device of any prior device claim, wherein the layer of uniform thickness sample is uniform over a lateral area that is in a range of 20 $mm^2$ to 100 $mm^2$.
30. The device of any prior device claim, wherein the layer of uniform thickness sample has a thickness uniformity of up to +/−5% or better.
31. The device of any prior device claim, wherein the layer of uniform thickness sample has a thickness uniformity of up to +/−10% or better.
32. The device of any prior device claim, wherein the layer of uniform thickness sample has a thickness uniformity of up to +/−20% or better.

33. The device of any prior device claim, wherein the layer of uniform thickness sample has a thickness uniformity of up to +/−30% or better.
34. The device of any prior device claim, wherein the layer of uniform thickness sample has a thickness uniformity of up to +/−40% or better.
35. The device of any prior device claim, wherein the layer of uniform thickness sample has a thickness uniformity of up to +/−50% or better.
36. The device of any prior device claim, wherein the spacers are pillars with a cross-sectional shape selected from round, polygonal, circular, square, rectangular, oval, elliptical, or any combination of the same.
37. The device of any prior device claim, wherein the spacers have pillar shape, have a substantially flat top surface, and have substantially uniform cross-section, wherein, for each spacer, the ratio of the lateral dimension of the spacer to its height is at least 1.
38. The device of any prior device claim, wherein the inter spacer distance is periodic.
39. The device of any prior device claim, wherein the spacers have a filling factor of 1% or higher, wherein the filling factor is the ratio of the spacer contact area to the total plate area.
40. The device of any prior device claim, wherein the Young's modulus of the spacers times the filling factor of the spacers is equal or larger than 20 MPa, wherein the filling factor is the ratio of the spacer contact area to the total plate area.
41. The device of any prior device claim, wherein the spacing between the two plates at the closed configuration is in less 200 um.
42. The device of any prior device claim, wherein the spacing between the two plates at the closed configuration is a value selected from between 1.8 um and 3.5 um.
43. The device of any prior device claim, wherein the spacing are fixed on a plate by directly embossing the plate or injection molding of the plate.
44. The device of any prior device claim, wherein the materials of the plate and the spacers are selected from polystyrene, PMMA, PC, COC, COP, or another plastic.
45. The device of any prior device claim, wherein the spacers have a pillar shape, and the sidewall corners of the spacers have a round shape with a radius of curvature at least 1 □m.
46. The device of any prior device claim, wherein the spacers have a density of at least $1000/mm^2$.
47. The device of any prior device claim, wherein at least one of the plates is transparent.
48. The device of any prior device claim, wherein the mold used to make the spacers is fabricated by a mold containing features that are fabricated by either (a) directly reactive ion etching or ion beam etched or (b) by a duplication or multiple duplication of the features that are reactive ion etched or ion beam etched.
49. The devices or methods of any prior embodiment, wherein the spacers are configured, such that the filling factor is in the range of 1% to 5%.

The devices or methods of any prior embodiment, wherein the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

50. The devices or methods of any prior embodiment, wherein the spacers are configured, such that the filling factor is in the range of 1% to 5%.
51. The devices or methods of any prior embodiment, wherein the spacers are configured, such that the filling factor is in the range of 5% to 10%.
52. The devices or methods of any prior embodiment, wherein the spacers are configured, such that the filling factor is in the range of 10% to 20%.
53. The devices or methods of any prior embodiment, wherein the spacers are configured, such that the filling factor is in the range of 20% to 30%.
54. The devices or methods of any prior embodiment, wherein the spacers are configured, such that the filling factor is 5%, 10%, 20%, 30%, 40%, 50%, or in a range of any two of the values.
55. The devices or methods of any prior embodiment, wherein the spacers are configured, such that the filling factor is 50%, 60%, 70%, 80%, or in a range of any two of the values.
56. The devices or methods of any prior embodiment, wherein the spacers are configured, such that the filling factor multiplies the Young's modulus of the spacer is in the range of 2 MPa and 10 MPa.
57. The devices or methods of any prior embodiment, wherein the spacers are configured, such that the filling factor multiplies the Young's modulus of the spacer is in the range of 10 MPa and 20 MPa.
58. The devices or methods of any prior embodiment, wherein the spacers are configured, such that the filling factor multiplies the Young's modulus of the spacer is in the range of 20 MPa and 40 MPa.
59. The devices or methods of any prior embodiment, wherein the spacers are configured, such that the filling factor multiplies the Young's modulus of the spacer is in the range of 40 MPa and 80 MPa.
60. The devices or methods of any prior embodiment, wherein the spacers are configured, such that the filling factor multiplies the Young's modulus of the spacer is in the range of 80 MPa and 120 MPa.
61. The devices or methods of any prior embodiment, wherein the spacers are configured, such that the filling factor multiplies the Young's modulus of the spacer is in the range of 120 MPa to 150 MPa.
62. The devices or methods of any prior embodiment, wherein the device further comprises a dry reagent coated on one or both plates.
63. The devices or methods of any prior embodiment, wherein the device further comprises, on one or both plates, a dry binding site that has a predetermined area, wherein the dry binding site binds to and immobilizes an analyte in the sample.
64. The devices or methods of any prior embodiment, wherein the device further comprises, on one or both plates, a releasable dry reagent and a release time control material that delays the time that the releasable dry regent is released into the sample.
65. The device of any prior embodiment, wherein the release time control material delays the time that the dry regent starts is released into the sample by at least 3 seconds.
66. The device of any prior embodiment, wherein the regent comprises anticoagulant and/or staining reagent(s)
67. The device of any prior embodiment, wherein the reagent comprises cell lysing reagent(s)
68. The devices or methods of any prior embodiment, wherein the device further comprises, on one or both plates, one or a plurality of dry binding sites and/or one or a plurality of reagent sites.
69. The device of any prior device embodiment, wherein the analyte comprises a molecule (e.g., a protein, peptides, DNA, RNA, nucleic acid, or other molecule), cells, tissues, viruses, and nanoparticles with different shapes.
70. The device of any prior device embodiment, wherein the analyte comprises white blood cells, red blood cells and platelets.
71. The device of any prior device embodiment, wherein the analyte is stained.
72. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.
73. The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.
74. The devices or methods of any prior embodiment, wherein for a flexible plate, the thickness of the flexible plate times the Young's modulus of the flexible plate is in the range 60 to 750 GPa-um.
75. The devices or methods of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$,
76. The devices or methods of any prior embodiment, wherein one or both plates comprises a location marker, either on a surface of or inside the plate, that provide information of a location of the plate.
77. The devices or methods of any prior embodiment, wherein one or both plates comprises a scale marker, either on a surface of or inside the plate, that provide information of a lateral dimension of a structure of the sample and/or the plate.
78. The devices or methods of any prior embodiment, wherein one or both plates comprises an imaging marker, either on surface of or inside the plate, that assists an imaging of the sample.
79. The devices or methods of any prior embodiment, wherein the spacers functions as a location marker, a scale marker, an imaging marker, or any combination of thereof.
80. The devices or methods of any prior embodiment, wherein the average thickness of the layer of uniform thickness is about equal to a minimum dimension of an analyte in the sample.
81. The devices or methods of any prior embodiment, wherein the inter-spacer distance is in the range of 7 $\square$m to 50 $\square$m.
82. The devices or methods of any prior embodiment, wherein the inter-spacer distance is in the range of 50 $\square$m to 120 $\square$m.
83. The devices or methods of any prior embodiment, wherein the inter-spacer distance is in the range of 120 $\square$m to 200 $\square$m (micron).
84. The devices or methods of any prior embodiment, wherein the inter-spacer distance is substantially periodic.
85. The devices or methods of any prior embodiment, wherein the spacers are pillars with a cross-sectional shape selected from round, polygonal, circular, square, rectangular, oval, elliptical, or any combination of the same.
86. The devices or methods of any prior embodiment, wherein the spacers have are pillar shape and have a substantially flat top surface, wherein, for each spacer, the ratio of the lateral dimension of the spacer to its height is at least 1.
87. The devices or methods of any prior embodiment, wherein each spacer has the ratio of the lateral dimension of the spacer to its height is at least 1.
88. The devices or methods of any prior embodiment, wherein the minimum lateral dimension of spacer is less than or substantially equal to the minimum dimension of an analyte in the sample.
89. The devices or methods of any prior embodiment, wherein the minimum lateral dimension of spacer is in the range of 0.5 um to 100 um.
90. The devices or methods of any prior embodiment, wherein the minimum lateral dimension of spacer is in the range of 0.5 um to 10 um.
91. The devices or methods of any prior embodiment, wherein the sample is blood.
92. The devices or methods of any prior embodiment, wherein the sample is whole blood without dilution by liquid.
93. The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
94. The devices or methods of any prior embodiment, wherein the sample is a biological sample, an environmental sample, a chemical sample, or clinical sample.
95. The devices or methods of any prior embodiment, wherein the spacers have a pillar shape, and the sidewall corners of the spacers have a round shape with a radius of curverture at least 1 $\square$m.
96. The devices or methods of any prior embodiment, wherein the spacers have a density of at least $100/mm^2$.
97. The devices or methods of any prior embodiment, wherein the spacers have a density of at least $1000/mm^2$.
98. The devices or methods of any prior embodiment, wherein at least one of the plates is transparent.
99. The devices or methods of any prior embodiment, wherein at least one of the plates is made from a flexible polymer.
100. The devices or methods of any prior embodiment, wherein, for a pressure that compresses the plates, the spacers are not compressible and/or, independently, only one of the plates is flexible.
101. The device of any of any prior embodiment, wherein the flexible plate has a thickness in the range of 10 um to 200 um.
102. The devices or methods of any prior embodiment, wherein the variation is less than 30%.
103. The devices or methods of any prior embodiment, wherein the variation is less than 10%.

104. The devices or methods of any prior embodiment, wherein the variation is less than 5%.
105. The devices or methods of any prior embodiment, wherein the first and second plates are connected and are configured to be changed from the open configuration to the closed configuration by folding the plates.
106. The devices or methods of any prior embodiment, wherein the first and second plates are connected by a hinge and are configured to be changed from the open configuration to the closed configuration by folding the plates along the hinge.
107. The devices or methods of any prior embodiment, wherein the first and second plates are connected by a hinge that is a separate material to the plates, and are configured to be changed from the open configuration to the closed configuration by folding the plates along the hinge
108. The devices or methods of any prior embodiment, wherein the first and second plates are made in a single piece of material and are configured to be changed from the open configuration to the closed configuration by folding the plates.
109. The devices or methods of any prior embodiment, wherein the layer of uniform thickness sample is uniform over a lateral area that is at least 1 mm$^2$.
110. The devices or methods of any prior embodiment, wherein the device is configured to analyze the sample in 60 seconds or less.
111. The devices or methods of any prior embodiment, wherein at the closed configuration, the final sample thickness device is configured to analyze the sample in 60 seconds or less.
112. The devices or methods of any prior embodiment, wherein at the closed configuration, the final sample thickness device is configured to analyze the sample in 10 seconds or less.
113. The devices or methods of any prior embodiment, wherein the dry binding site comprises a capture agent.
114. The devices or methods of any prior embodiment, wherein the dry binding site comprises an antibody or nucleic acid.
115. The devices or methods of any prior embodiment, wherein the releasable dry reagent is a labeled reagent.
116. The devices or methods of any prior embodiment, wherein the releasable dry reagent is a fluorescently-labeled reagent.
117. The devices or methods of any prior embodiment, wherein the releasable dry reagent is a fluorescently-labeled antibody.
118. The devices or methods of any prior embodiment, wherein the releasable dry reagent is a cell stain.
119. The devices or methods of any prior embodiment, wherein the releasable dry reagent is a cell lysing.
120. The devices or methods of any prior embodiment, wherein the detector is an optical detector that detects an optical signal.
121. The devices or methods of any prior embodiment, wherein the detector is an electric detector that detect electrical signal.
122. The device of any prior device embodiment, wherein the spacing are fixed on a plate by directly embossing the plate or injection molding of the plate.
123. The device of any prior device embodiment, wherein the materials of the plate and the spacers are selected from polystyrene, PMMA, PC, COC, COP, or another plastic.
124. A system for rapidly analyzing a sample using a mobile phone comprising:
    (a) a device of any prior embodiment;
    (b) a mobile communication device comprising:
        i. one or a plurality of cameras for the detecting and/or imaging the sample;
        ii. electronics, signal processors, hardware and software for receiving and/or processing the detected signal and/or the image of the sample and for remote communication; and
    (c) a light source from either the mobile communication device or an external source;
    wherein the detector in The devices or methods of any prior embodiment is provided by the mobile communication device, and detects an analyte in the sample at the closed configuration.
125. The system of any prior system embodiment, wherein one of the plates has a binding site that binds an analyte, wherein at least part of the uniform sample thickness layer is over the binding site, and is substantially less than the average lateral linear dimension of the binding site.
126. The system of any prior system embodiment, further comprising:
    (d) a housing configured to hold the sample and to be mounted to the mobile communication device.
127. The system of any prior system embodiment, wherein the housing comprises optics for facilitating the imaging and/or signal processing of the sample by the mobile communication device, and a mount configured to hold the optics on the mobile communication device.
128. The system of any prior system embodiment, wherein an element of the optics in the housing is movable relative to the housing.
129. The system of any prior system embodiment, wherein the mobile communication device is configured to communicate test results to a medical professional, a medical facility or an insurance company.
130. The system of any prior system embodiment, wherein the mobile communication device is further configured to communicate information on the test and the subject with the medical professional, medical facility or insurance company.
131. The system of any prior system embodiment, wherein the mobile communication device is further configured to communicate information of the test to a cloud network, and the cloud network process the information to refine the test results.
132. The system of any prior system embodiment, wherein the mobile communication device is further configured to communicate information of the test and the subject to a cloud network, the cloud network process the information to refine the test results, and the refined test results will send back the subject.
133. The system of any prior system embodiment, wherein the mobile communication device is configured to receive a prescription, diagnosis or a recommendation from a medical professional.
134. The system of any prior system embodiment, wherein the mobile communication device is configured with hardware and software to:
    (a) capture an image of the sample;
    (b) analyze a test location and a control location in in image; and
    (c) compare a value obtained from analysis of the test location to a threshold value that characterizes the rapid diagnostic test.
135. The system of any prior system embodiment, wherein at least one of the plates comprises a storage site in which assay reagents are stored.

136. The system of any prior system embodiment, at least one of the cameras reads a signal from the device.
137. The system of any prior system embodiment, wherein the mobile communication device communicates with the remote location via a wifi or cellular network.
138. The system of any prior system embodiment, wherein the mobile communication device is a mobile phone.
139. A method for rapidly analyzing an analyte in a sample using a mobile phone, comprising:
(a) depositing a sample on the device of any prior system embodiment;
(b) assaying an analyte in the sample deposited on the device to generate a result; and
(c) communicating the result from the mobile communication device to a location remote from the mobile communication device.
140. The method of any prior embodiments embodiment, wherein the analyte comprises a molecule (e.g., a protein, peptides, DNA, RNA, nucleic acid, or other molecule), cells, tissues, viruses, and nanoparticles with different shapes.
141. The method of any prior embodiment, wherein the analyte comprises white blood cell, red blood cell and platelets.
142. The method of any prior embodiment, wherein the assaying comprises performing a white blood cells differential assay.
143. The method of any prior embodiments embodiment, wherein the method comprises:
analyzing the results at the remote location to provide an analyzed result; and
communicating the analyzed result from the remote location to the mobile communication device.
144. The method of any prior embodiment, wherein the analysis is done by a medical professional at a remote location.
145. The method of any prior embodiment, wherein the mobile communication device receives a prescription, diagnosis or a recommendation from a medical professional at a remote location.
146. The method of any prior embodiment, wherein the sample is a bodily fluid.
147. The method of any prior embodiment, wherein the bodily fluid is blood, saliva or urine.
148. The method of any prior embodiment, wherein the sample is whole blood without dilution by a liquid.
149. The method of any prior embodiment, wherein the assaying step comprises detecting an analyte in the sample.
150. The method of any prior embodiment, wherein the analyte is a biomarker.
151. The method of any prior embodiment, wherein the analyte is a protein, nucleic acid, cell, or metabolite.
152. The method of any prior embodiment, wherein the method comprises counting the number of red blood cells.
153. The method of any of any prior embodiment, wherein the method comprises counting the number of white blood cells.
154. The method of any prior embodiment, wherein method comprises staining the cells in the sample and counting the number of neutrophils, lymphocytes, monocytes, eosoniphils and basophils.
155. The method of any prior embodiments embodiment, wherein the assay done in step (b) is a binding assay or a biochemical assay.
156. A method for analyzing a sample comprising:
obtaining a device of any prior device embodiment;
depositing the sample onto one or both pates of the device;
placing the plates in a closed configuration and applying an external force over at least part of the plates; and
analyzing the in the layer of uniform thickness while the plates are the closed configuration.
157. The devices or methods of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.
158. The devices or methods of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
159. The devices or methods of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
160. The devices or methods of any prior embodiment, wherein the analyte assay area is between a pair of electrodes.
161. The devices or methods of any prior embodiment, wherein the assay area is defined by a patch of dried reagent.
162. The devices or methods of any prior embodiment, wherein the assay area binds to and immobilizes the analyte
163. The devices or methods of any prior embodiment, wherein the assay area is defined by a patch of binding reagent that, upon contacting the sample, dissolves into the sample, diffuses in the sample, and binds to the analyte.
164. The devices or methods of any prior embodiment, wherein the inter-spacer distance is in the range of 14 □m to 200 □m.
165. The devices or methods of any prior embodiment, wherein the inter-spacer distance is in the range of 7 □m to 20 □m.
166. The devices or methods of any prior embodiment, wherein the spacers are pillars with a cross-sectional shape selected from round, polygonal, circular, square, rectangular, oval, elliptical, or any combination of the same.
167. The devices or methods of any prior embodiment, wherein the spacers have are pillar shape and have a substantially flat top surface, wherein, for each spacer, the ratio of the lateral dimension of the spacer to its height is at least 1.

168. The devices or methods of any prior embodiment, wherein the spacers have a pillar shape, and the sidewall corners of the spacers have a round shape with a radius of curverture at least 1 □m.
169. The devices or methods of any prior embodiment, wherein the spacers have a density of at least 1000/mm².
170. The devices or methods of any prior embodiment, wherein at least one of the plates is transparent.
171. The devices or methods of any prior embodiment, wherein at least one of the plates is made from a flexible polymer.
172. The devices or methods of any prior embodiment, wherein only one of the plates is flexible.
The device of any prior embodiment, wherein the area-determination device is a camera.
The area-determination device comprises an area in the sample contact area of a plate, wherein the area is less than 1/100, 1/20, 1/10, 1/6, 1/5, 1/4, 1/3, 1/2, 2/3 of the sample contact area, or in a range between any of the two values.
The area-determination device comprises a camera and an area in the sample contact area of a plate, wherein the area is in contact with the sample.
The devices or methods of any prior embodiment, wherein the deformable sample comprises a liquid sample.
The devices or methods of any prior embodiment, wherein the imprecision force has a variation at least 30% of the total force that actually is applied.
The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.
173. The device of any prior embodiment, wherein spacers have a flat top.
174. The device of any prior embodiment, wherein the device is further configured to have, after the pressing force is removed, a sample thickness that is substantially the same in thickness and uniformity as that when the force is applied.
175. The device of any prior embodiment, wherein the imprecise force is provided by human hand.
176. The device of any prior embodiment, wherein the inter spacer distance is substantially constant.
177. The device of any prior embodiment, wherein the inter spacer distance is substantially periodic in the area of the uniform sample thickness area.
178. The device of any prior embodiment, wherein the multiplication product of the filling factor and the Young's modulus of the spacer is 2 MPa or larger.
179. The device of any prior embodiment, wherein the force is applied by hand directly or indirectly.
180. The device of any prior embodiment, wherein the force applied is in the range of 1 N to 20 N.
181. The device of any prior embodiment, wherein the force applied is in the range of 20 N to 200 N.
182. The device of any prior embodiment wherein the highly uniform layer has a thickness that varies by less than 15%, 10%, or 5% of an average thickness.
183. The device of any prior embodiment, wherein the imprecise force is applied by pinching the device between a thumb and forefinger.
184. The device of any prior embodiment, wherein the predetermined sample thickness is larger than the spacer height.
185. The device of any prior embodiment, wherein the device holds itself in the closed configuration after the pressing force has been removed.
186. The device of any prior embodiment, wherein the uniform thickness sample layer area is larger than that area upon which the pressing force is applied.
187. The device of any prior embodiment, wherein the spacers do not significantly deform during application of the pressing force.
188. The device of any prior embodiment, wherein the pressing force is not predetermined beforehand and is not measured.
189. In some embodiments, the fluidic sample is replaced by a deformable sample and the embodiments for making at least a part of the fluidic sample into a uniform thickness layer can make at least a part of the deformable sample into a uniform thickness layer.
190. The devices and methods of any prior device claim, wherein the inter spacer distance is periodic.
191. The devices and methods of any prior device claim, wherein the spacers have a flat top.
192. The devices and methods of any prior device claim, wherein the inter spacer distance is at least two times large than the size of the targeted analyte in the sample.

Manufacturing of Q-Card

MA1. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam;
  ii. the second plate is 10 um to 250 um thick and comprises, on its inner surface, (a) a sample contact area for contacting a sample, and (b) spacers on the sample contact area;
  iii. the hinge that connect the first and the second plates; and
wherein the first and second plate are movable relative to each other around the axis of the hinge.

MA2. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area;
  ii. the second plate, that is 10 nm to 250 nm thick, comprises, on its inner surface, a sample contact area for contacting a sample;
  iii. the hinge that connect the first and the second plates; and
wherein the first and second plate are movable relative to each other around the axis of the hinge.

MA3. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) spacers on the sample contact area;
  ii. the second plate, that is 10 um to 250 um thick, comprises, on its inner surface, (a) a sample contact area for contacting a sample, and (b) a sample overflow dam that surrounds the sample contact area is configured to present a sample flow outside of the dam, and;
  iii. the hinge that connect the first and the second plates; and
wherein the first and second plate are movable relative to each other around the axis of the hinge.

MA4 An embodiment of the Q-Card comprising: a first plate, a second plate, and a hinge, wherein
  i. the first plate, that is about 200 nm to 1500 nm thick, comprises, on its inner surface, a sample contact area for contacting a sample;
  ii. the second plate, that is 10 um to 250 um thick, comprises, on its inner surface, (a) a sample contact area for contacting a sample, (b) a sample overflow dam that surrounds the sample contact area is configured to present a sample flow outside of the dam, and (c) spacers on the sample contact area; and
  iii. the hinge that connect the first and the second plates; and
wherein the first and second plate are movable relative to each other around the axis of the hinge.
M1 An embodiment of a method for fabricating the Q-Card of any embodiments of MA1 to MA4, comprising:
  (a) injection molding of the first plate,
  (b) nanoimprinting or extrusion printing of the second plate.
M2 An embodiment of a method for fabricating the Q-Card of any embodiments of MA1 to MA4, comprising:
  (a) Laser cutting the first plate,
  (b) nanoimprinting or extrusion printing of the second plate.
M3 An embodiment of a method for fabricating the Q-Card of any embodiments of MA1 to MA4, comprising:
  (a) Injection molding and laser cutting the first plate,
  (b) nanoimprinting or extrusion printing of the second plate.
M4 An embodiment of a method for fabricating the Q-Card of any embodiments of MA1 to MA4, comprising: nanoimprinting or extrusion printing to fabricated both the first and the second plate.
M5 An embodiment of a method for fabricating the Q-Card of any embodiments of MA1 to MA4, comprising: fabricating the first plate or the second plate, using injection molding, laser cutting the first plate, nanoimprinting, extrusion printing, or a combination of thereof.
The method of any embodiments of M1-M5, wherein the method further comprises a step of attach the hinge on the first and the second plates after the fabrication of the first and second plates.

B. QMAX DEVICE WITH DIFFERENT SPACER HEIGHTS

B-1. Examples of QMAX Device with Different Spacer Heights

One aspect of the present invention provides a QMAX device for analyzing a liquid sample, which comprises spacers of different heights.

Figure 3:
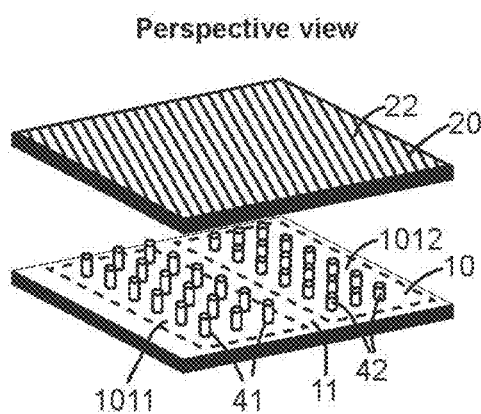
FIG. 3 illustrates an embodiment of a QMAX device that comprises two sets of spacers, each of which has a uniform height that is different from that of the other set. Panel (A) shows a prospective view of a first plate, a second plate and spacers; panel (B) shows prospective and sectional views of depositing a sample on one of the plates; panel (C) shows using the first plate and the second plate to compress the sample into a layer of uniform thickness, which is regulated by the height of the spacers.
Figure 3:
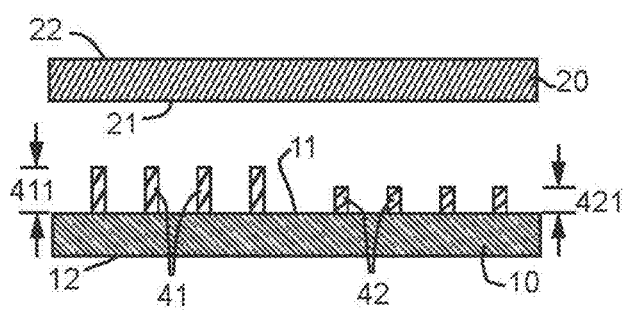
Figure 3:
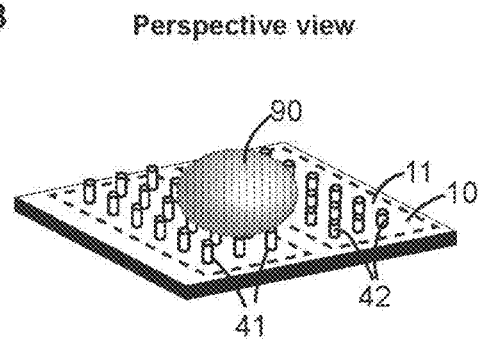
Figure 3:
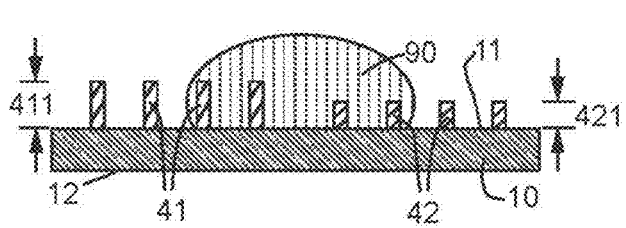
Figure 3:
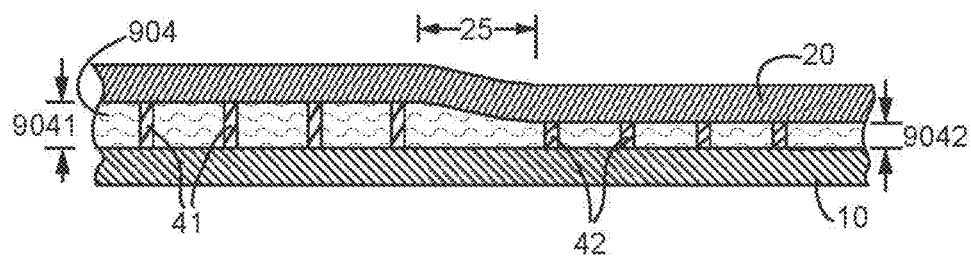

FIG. 3 schematically shows one embodiment of the QMAX device, which comprises a first plate 10 and a second plate 20. In particular, panel (A) shows both the perspective and cross-sectional views of the first plate 10 and the second plate 20. Each of the plates respectively comprises an inner surface (11 and 21) and an outer surface (12 and 22). The first plate 10 has, on its inner surface 11, a first sample contact area 1011 at one location and a second sample contact area 1012 at another location. The second plate 20 also has, on its inner surface 21, a first and a second sample contact area (not shown) that are corresponding to the first sample contact area 1011 and the second sample contact area 1012 of the first plate, respectively. (The meaning of "corresponding" is discussed in details below). The sample contact areas are for contacting a sample to be analyzed using the device. Further, as illustrated, the first plate 10 comprises a plurality of spacers (41 and 42). It should be noted, however, in some embodiments, the second plate 20 or both the first plate 10 and second plate 20 have the spacers on the respective inner surfaces. In some embodiments, the spacers (42 and 42) are fixed to one or both of the plates 10 and 20. Herein the term "fixed" means that the spacers are attached to a plate and the attachment is maintained during one or more uses of the plate.

In some embodiments, the QMAX device in the present invention include but not be limited to the QMAX device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

In some embodiments, there are at least one of the spacers inside the first sample contact area 1011 and the second sample contact area 1012, respectively. As illustrated in FIG. 3, the spacers 41 and 42 are inside the first sample contact area 1011 and the second sample contact area 1012, respectively. The spacers over the first sample contact area 41 (hereinafter "the first set of spacers") have a first uniform height 411 and a uniform inter-spacer distance, and so do the spacers over the second sample contact area 42 (hereinafter "the second set of spacers"). In some embodiments, the first uniform height 411 is different from the second uniform height 421 of the second set of spacers 42. In some embodiments, the first or the second uniform height is 10 nm or more, 20 nm or more, 50 nm or more, 100 nm or more, 200 nm or more, 500 nm or more, 1 □m or more, 2 □m or more, 5 □m or more, 10 □m or more, 20 □m or more, 50 □m or more, 100 □m or more, 200 □m or more, 500 □m or more, 1 mm or more, 750 ⊐m or less, 250 □m or less, 150 □m or less, 75 □m or less, 25 □m or less, 15 □m or less, 7.5 □m or less, 1.5 □m or less, 750 nm or less, 250 nm or less, 150 nm or less, 75 nm or less, 25 nm or less, or 15 nm or less. In some embodiments, the difference between the first and second uniform heights is 5 nm or more, 10 nm or more, 20 nm or more, 50 nm or more, 100 nm or more, 200 nm or more, 500 nm or more, 1 □m or more, 2 □m or more, 5 □m or more, 10 □m or more, 20 □m or more, 50 ⊏ m or more, 100 □m or more, 200 □m or more, 500 □m or more, 1 mm or more, 750 □m or less, 250 □m or less, 150 □m or less, 75 □m or less, 25 □m or less, 15 □m or less, 7.5 □m or less, 1.5 □m or less, 750 nm or less, 250 nm or less, 150 nm or less, 75 nm or less, 25 nm or less, 15 nm or less, or 7.5 nm or less.

In some embodiments, the spacers have a constant inter-spacer distance. In some embodiments, the first set spacers have a first constant inter-spacer distance, the second set spacers have a different second constant inter-spacer distance. In some embodiments, the constant inter-spacer distance is 10 nm or more, 20 nm or more, 50 nm or more, 100 nm or more, 200 nm or more, 500 nm or more, 1 µm or more, 2 µm or more, 5 µm or more, 10 µm or more, 20 µm or more, 50 µm or more, 100 µm or more, 200 µm or more, 500 µm or more, 1 mm or more, 750 µm or less, 250 µm or less, 150 µm or less, 75 µm or less, 25 µm or less, 15 µm or less, 7.5 µm or less, 1.5 µm or less, 750 nm or less, 250 nm or less, 150 nm or less, 75 nm or less, 25 nm or less, or 15 nm or less. In some embodiments, the constant inter-spacer distance is at least 2 times larger than the size of the target analyte. In some embodiments, the constant inter-spacer distance is up to 200 µm.

FIG. 3 further illustrates that the first plate 10 and the second plate 20 are movable relative to each other into different configurations, including an open configuration and a closed configuration. FIG. B1 panels (A) and (B) depict some embodiments of the open configuration. In the open configuration, the two plates are partially or entirely separated apart, and the spacing between the plates is not regulated by the spacers (41 and 42). As shown in panel (B), the spacing between the plates in the open configuration allows the sample 90 to be deposited on the first plate 10. It is to be noted, however, in some embodiments, the sample 90 is deposited either on the second plate 20 or on both plates 10 and 20.

FIG. 3 panel (C) shows the exemplary embodiment of the closed configuration of the two plates, that is configured after the sample deposition as exemplified in FIG. 3 panel (B). In the closed configuration, the two plates are brought to face each other with their inner surfaces 11 and 21. Consequently, at least part of the deposited sample 90 is compressed by the two plates into a layer 904. The layer 904, as shown in the figure, has a first uniform thickness 9041 at the first sample contact area 1011 (not indicated) and a second uniform thickness 9042 at the second sample contact area 1012 (not indicated). In some embodiments, the first and second uniform thickness 9041 and 9042 are regulated by the first and second sets of the spacers 41 and 42, respectively. In some embodiments, the first uniform thickness 9041 is different from the second uniform thickness 9042. It is to be noted that the term "layer of uniform thickness" as used herein refers to a layer of sample that has a uniform thickness across a continuous substantial lateral area thereof, and the uniform thickness is different in one substantial lateral area from another. In some embodiments, the percentage of the whole lateral area of the layer that the substantial lateral area takes up is equal to or more than 10%, 20%, 30%, 40%, 50%, 60%, 70%, 80%, 90%, 95%, 99%, 100%, or a range between any two of the values.

In some embodiments, the respectively corresponding sample contact areas are over one another in the closed configuration, meaning that the first sample contact area on the first plate and its corresponding first sample contact area on the second plate are configured to face each other in the closed configuration and so do the corresponding second sample contact areas on the first and the second plates. The term "corresponding" as used herein in certain contexts of the QMAX device, refers to the relationship between a pair of the subjects (e.g. first or second sample contact area, the binding site, storage site) belonging to each of the two plates of the QMAX device, respectively, that face each other in the closed configuration.

Figure 4:
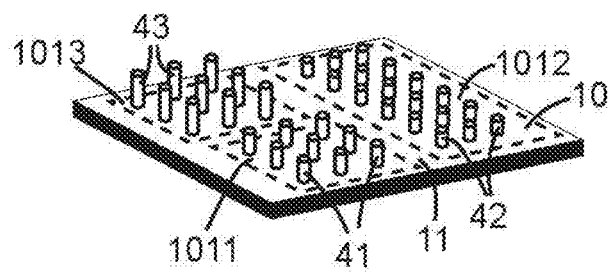
FIG. 4 shows two exemplary embodiments of a QMAX device for analyzing a liquid sample provided by the present invention. Panel (A) shows a device comprising three sets of spacers, each of which has a uniform height that is different from that of other sets, panel (B) shows a device comprising four sets of spacers, each of which has a uniform height that is different from that of other sets.
Figure 4:
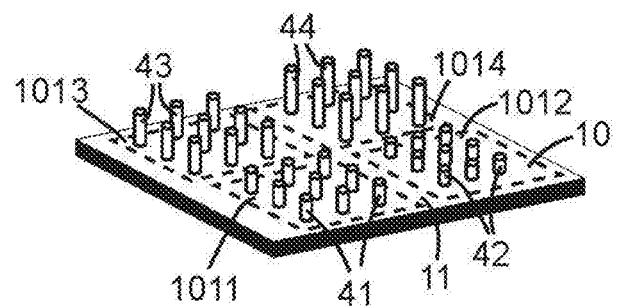
Figure 5:
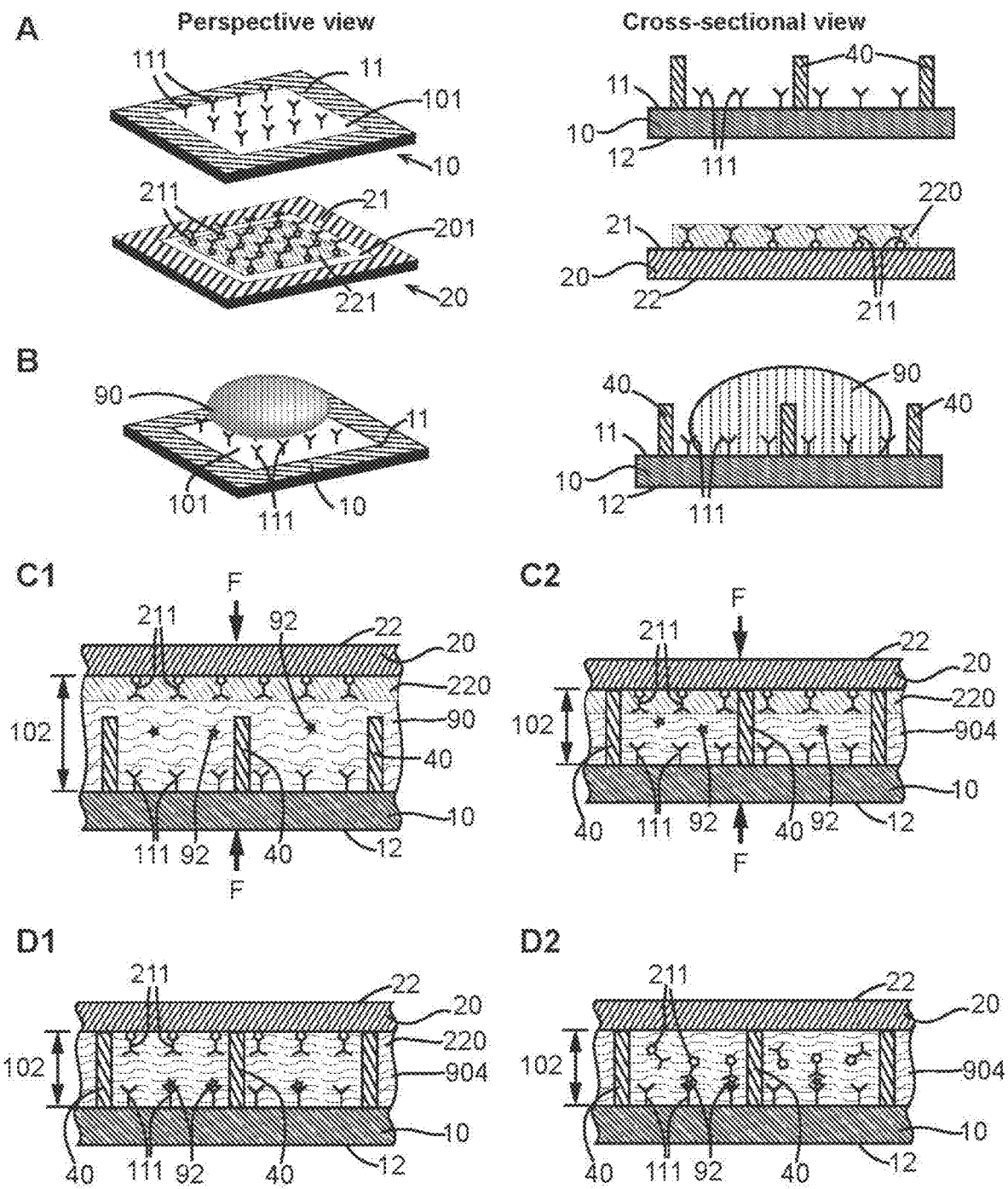
FIG. 5 illustrates an embodiment of a QMAX device that comprises a slow release agent that is coated on top of the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panels (D1) and (D2) show the delayed release of the detection agent until the binding of the target analyte by the binding agent and the consequential binding of the target analyte by the detection agent in the thin layer. The delayed release is controlled by the slow release material.
Figure 6:
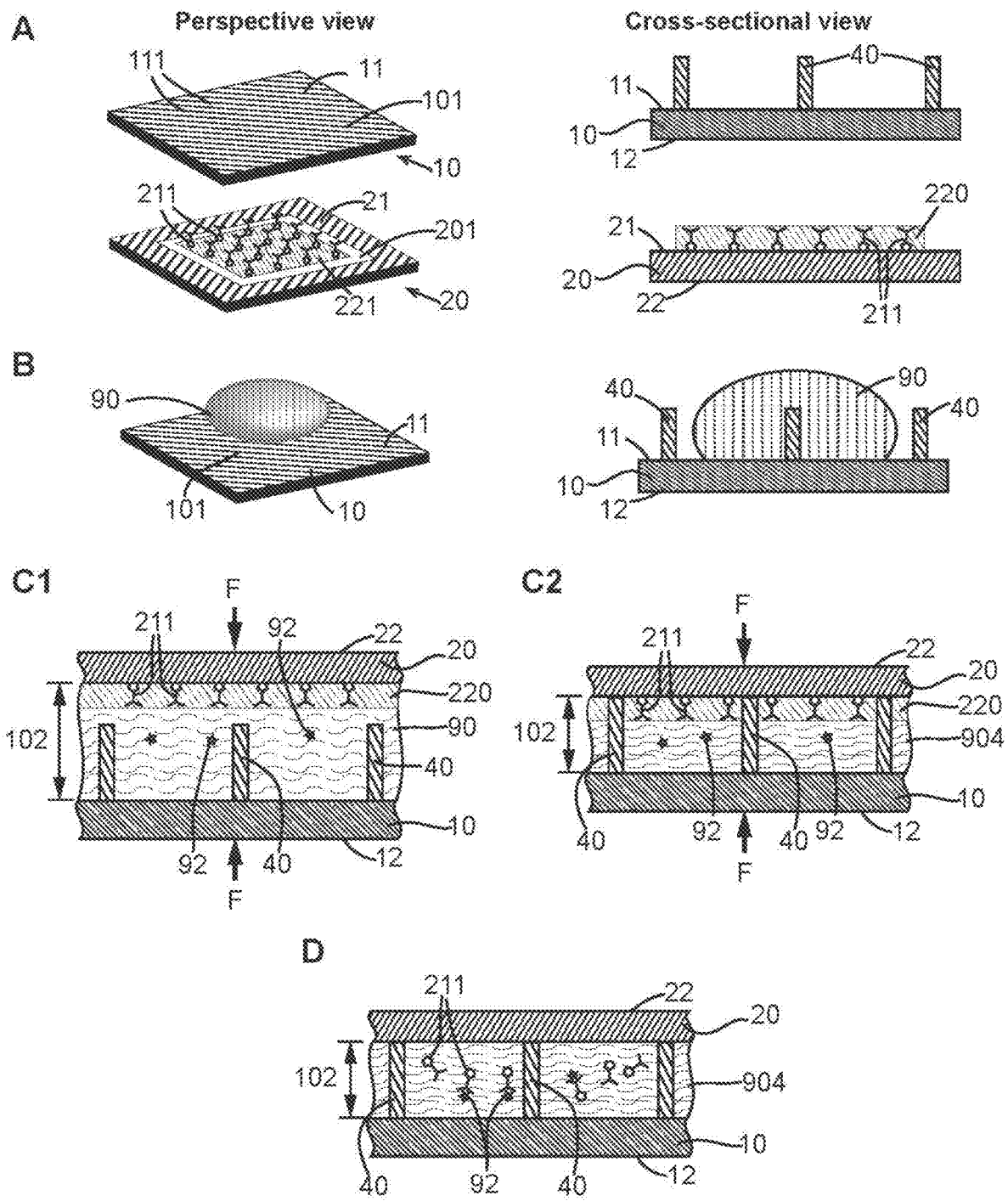
FIG. 6 illustrates an embodiment of a QMAX device that comprises a slow release agent that is coated on top of the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panel (D) show the delayed release of the detection agent until the formation of the thin layer and the consequential binding of the target analyte by the detection agent in the thin layer. The delayed release is controlled by the slow release material.
Figure 7:
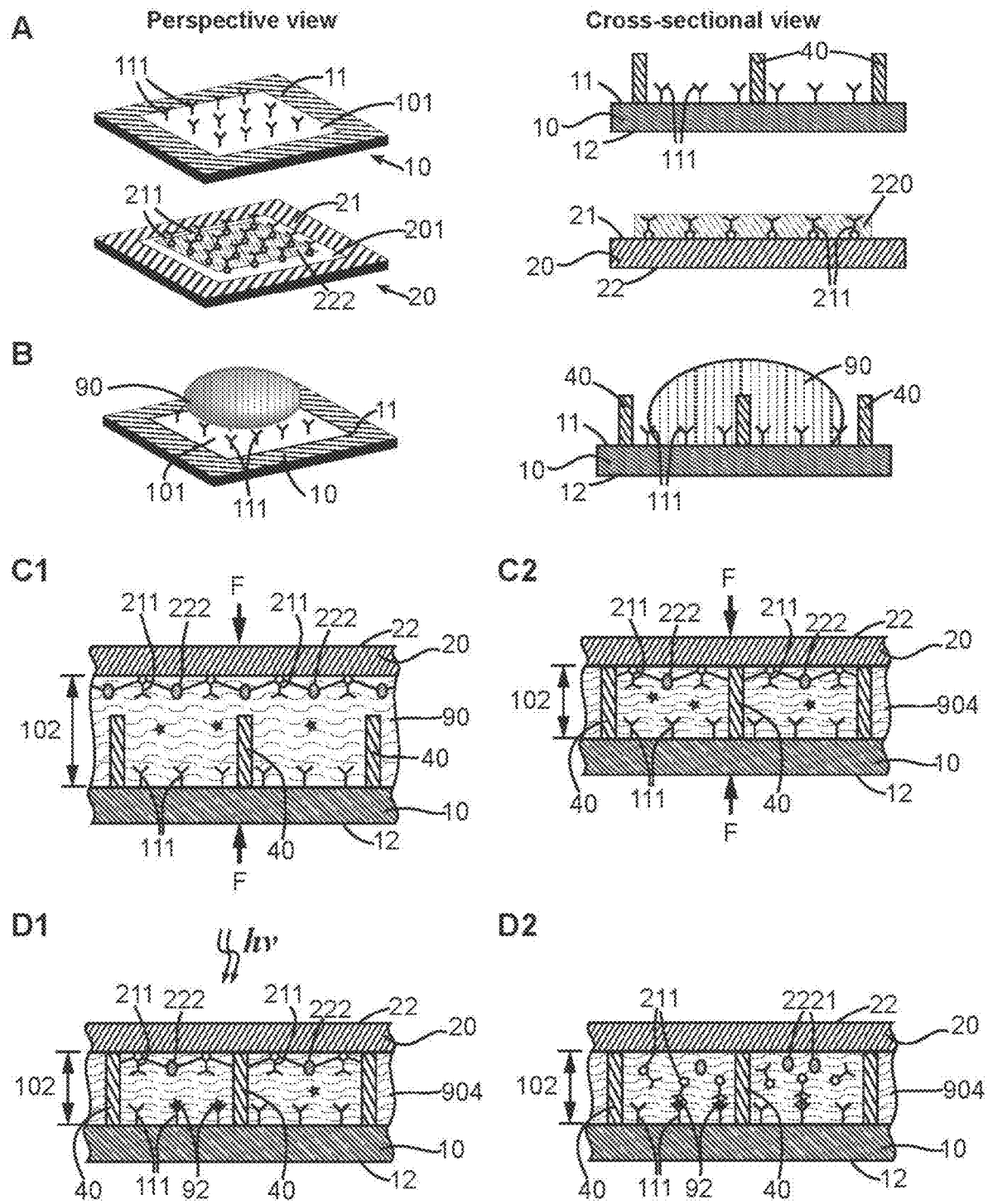
FIG. 7 illustrates an embodiment of a QMAX device that comprises a stimulus-sensitive release agent that is mixed with the detection agent on the plate. Panel (A) shows a prospective view of a first plate, a second plate and spacers; panel (B) shows prospective and sectional views of depositing a sample on one of the plates; panels (C1) and (C2) show using the first plate and the second plate to compress the sample into a thin layer, which is regulated by the height of the spacers; and panels (D1) and (D2) show the controlled release of the detection agent and the consequential binding of the target analyte by the detection agent in the thin layer. The release of the detection agent is controlled by the delivery of a laser beam on the stimulus-sensitive release agent.
Figure 8:
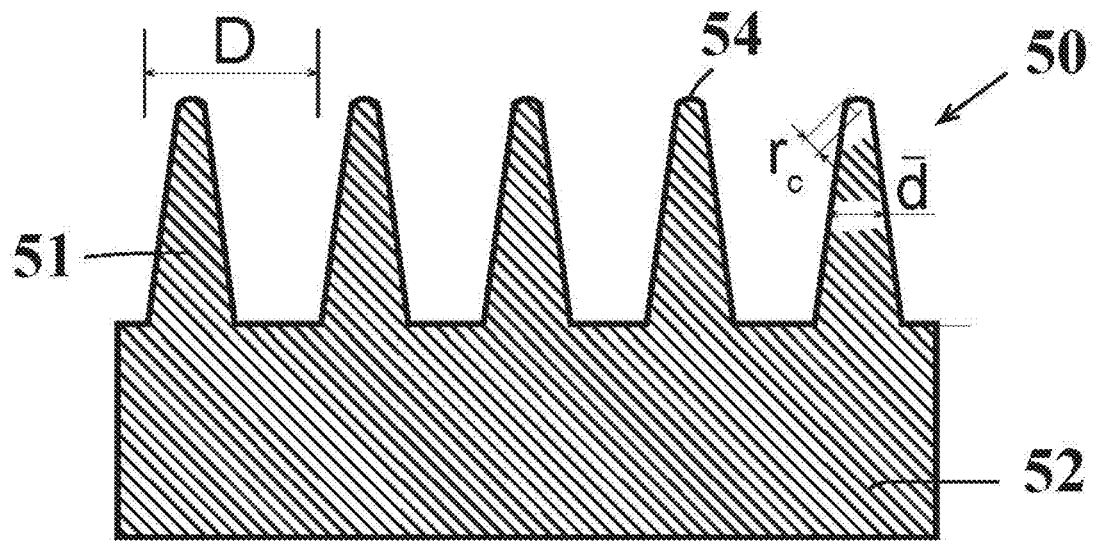
FIGS. 8 and 9 schematically illustrate a cross-sectional and a top view of L-plate according to one exemplary embodiment of the present invention, respectively.
Figure 9:
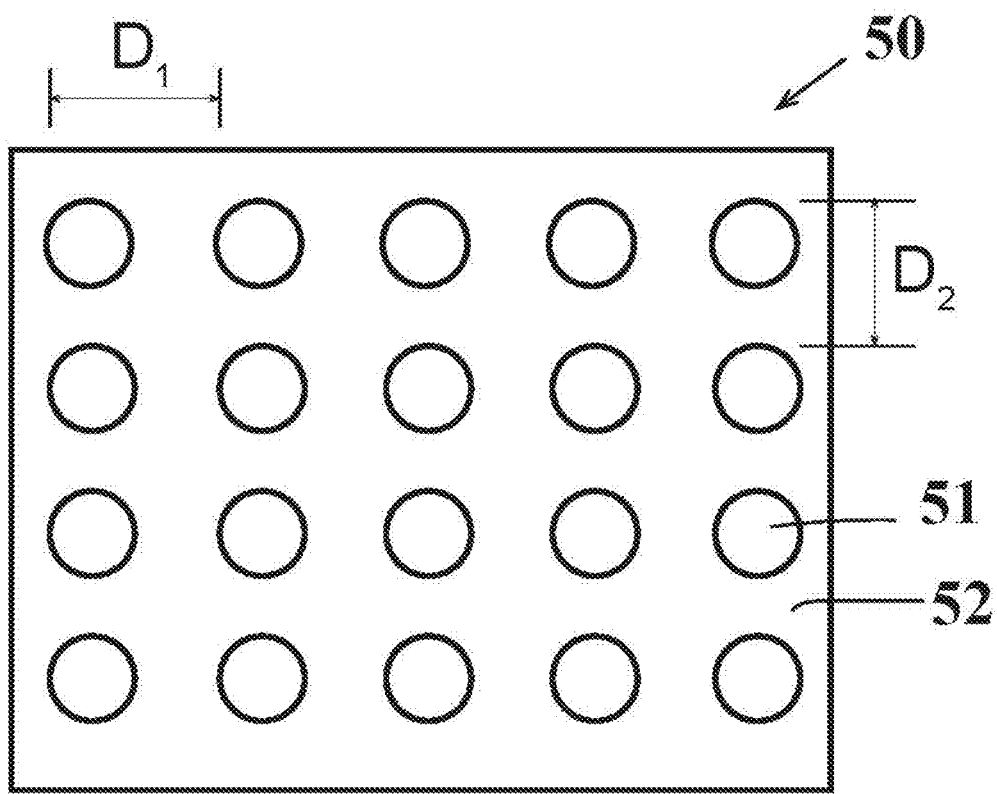
Figure 10:
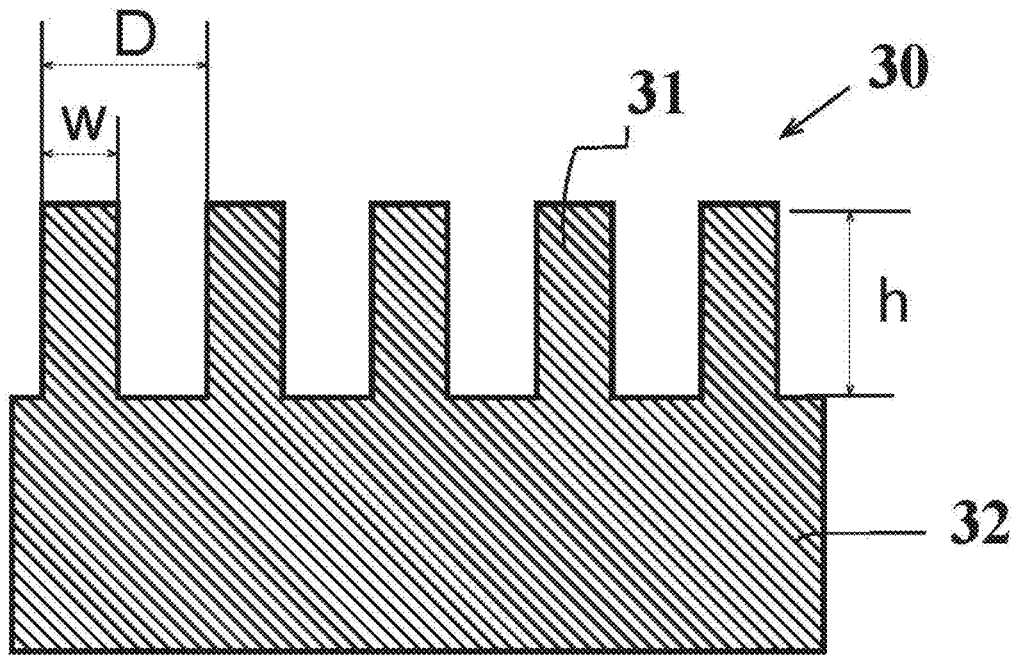
FIGS. 10 and 11 schematically illustrate a cross-sectional and a top view of L-plate according to another exemplary embodiment of the present invention, respectively.
Figure 11:
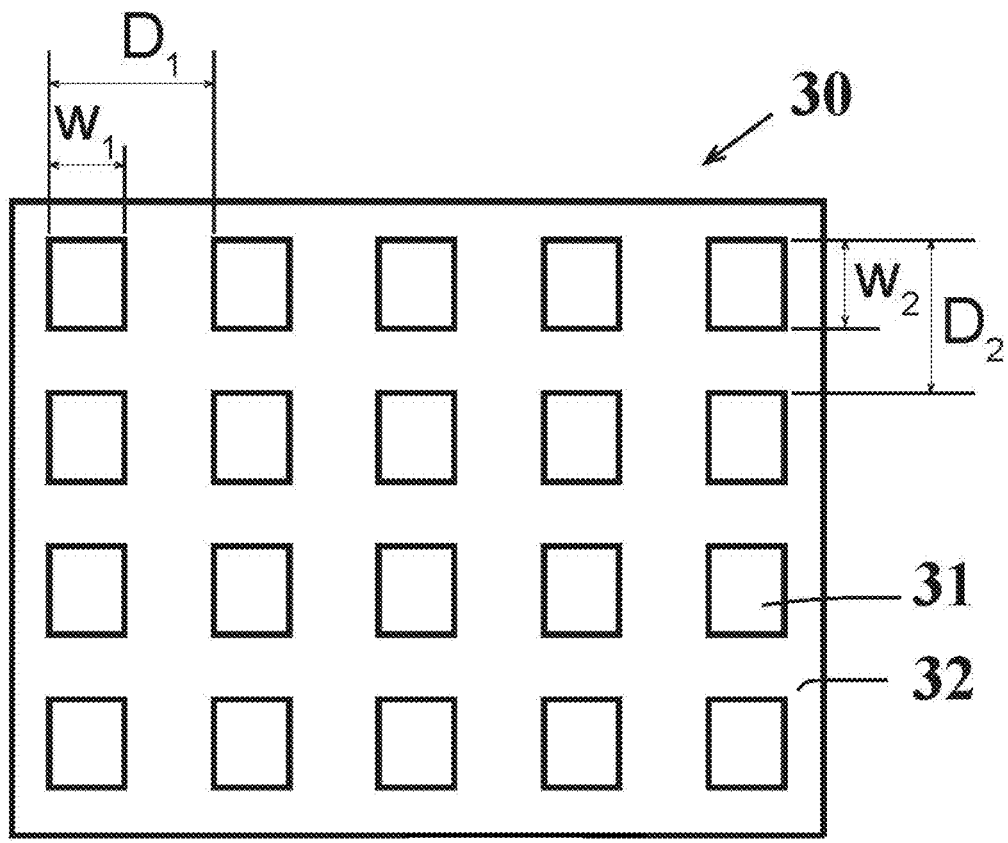
Figure 12:
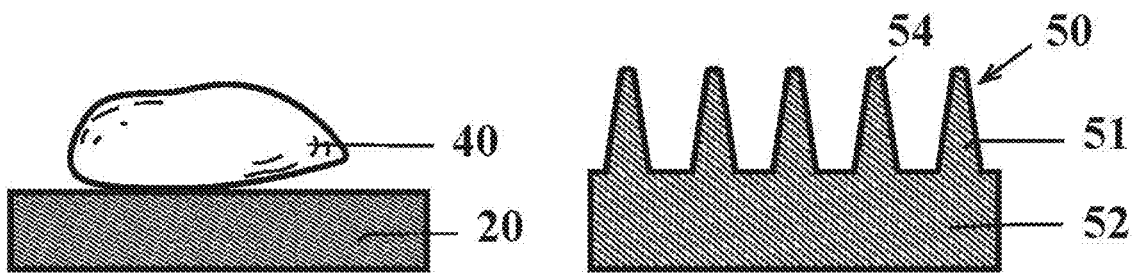
FIGS. 12-15 schematically illustrate the cell lysis process using L-plate and substrate plate according to some embodiments of the present invention.
Figure 13:
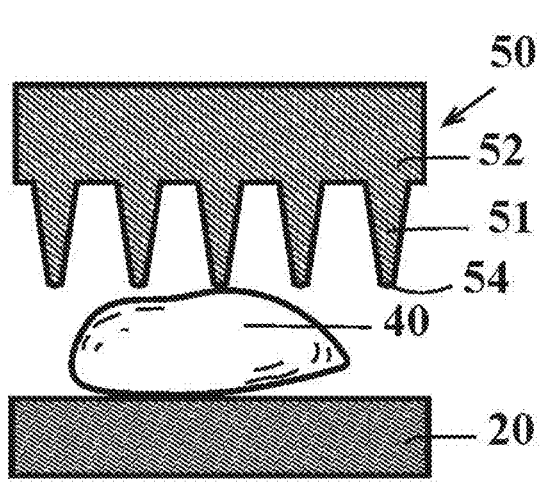
Figure 14:
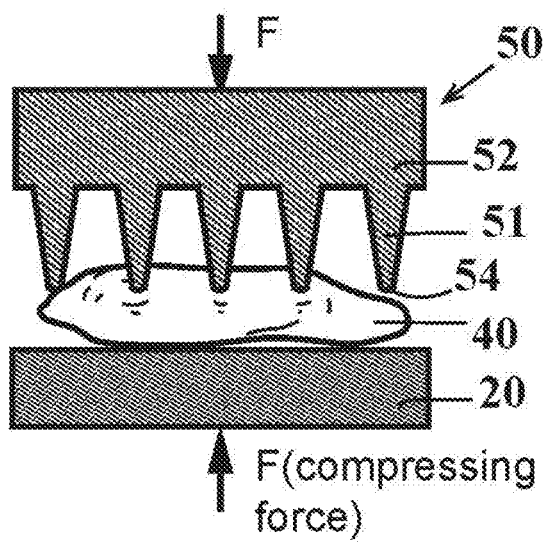
Figure 15:
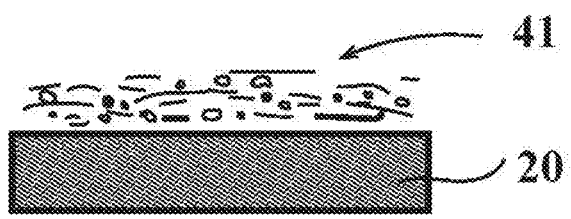

FIG. 4 shows some exemplary embodiments of the device provided by the present invention. As shown in the figure, the device comprises more than two sample contact areas on the first plate 10. Panel (A) shows that the first plate 10 has a first sample contact area 1011, a second contact area 1012, and a third sample contact area 1013. In each sample contact area, there is at least one spacer respectively. Here, spacers 41, 42, and 42 are in the sample contact areas 1011, 1012, and 1013, respectively. In some embodiments, all the three sets of spacers have a respective uniform height that is different from one another. Panel (B) shows another exemplary device, wherein there are four sample contact areas (1011, 1012, 1013, and 1014) and four sets of spacers of different uniform heights (41, 42, 43, and 44). In other embodiments, it is also possible that the number of sample contact areas the device comprises is equal to or more than 5, 6, 7, 8, 9, 10, 20, 30, 50, 75, 100, 200, 500, 1000, or in a range between any two of the values.

In some embodiments, one or both of the first plate 10 and second plate 20 are flexible, in order to enable the formation of the layer of uniform thickness 904 that has different uniform thicknesses at different sample contact areas.

In some embodiments, the distance between two neighboring spacer sets is 10 nm or more, 20 nm or more, 50 nm or more, 100 nm or more, 200 nm or more, 500 nm or more, 1 µm or more, 2 µm or more, 5 µm or more, 10 µm or more, 20 µm or more, 50 µm or more, 100 µm or more, 200 µm or more, 500 µm or more, 1 mm or more, 750 µm or less, 250 µm or less, 150 µm or less, 75 µm or less, 25 µm or less, 15 µm or less, 7.5 µm or less, 1.5 µm or less, 750 nm or less, 250 nm or less, 150 nm or less, 75 nm or less, 25 nm or less, or 15 nm or less. The term "spacer set" as used herein refers to a group of consecutive spacers having a uniform height, wherein the uniform height is different from that of other spacers on the same QMAX device, for instance, as described above, the first spacer set or the first set of spacers 41 have a first uniform height 411 that is different from the second uniform height 421 of the second spacer set 42. The term "the distance between two neighboring spacer sets" is defined as the minimum distance between two spacers from each of the two neighboring spacer sets. In some embodiments, the distance between two neighboring spacer sets and the flexibility of the two plates are designed in a way that in the closed configuration, part of the sample can be compressed into a layer of uniform thickness that has different and uniform thicknesses at different sample contact areas. In some embodiments, distance between two neighboring spacer sets and the flexibility of the two plates are designed in a way that at any given location of the two plates, the spacing between the two plates is only regulated by the local spacers, but not affected by remote spacers. Consequently, the uniform thickness of the layer across the lateral dimension of the plate is all regulated by the spacers.

In some embodiments, it would be possible to conformable press, either in parallel or sequentially, the QMAX device into a closed configuration. Conformable pressing is a method that makes the pressure applied over an area to be substantially constant regardless of the shape variation of the outer surfaces of the plates; In particular, parallel conformable pressing applies the pressures on the intended area at the same time, and sequential conformable pressing applies the pressure on a part of the intended area and gradually move to other area. Conformable pressing can be applied by human hand, air blow, liquid pressure, or other forces.

In some embodiments, the QMAX device is self-held in the closed configuration after removing the external force that brings the device from an open configuration to the closed configuration. The "self-holding" may be due to the forces existing between the inner surfaces of the two plates than the external force, such as, but not limited to capillary force. In some embodiments, the thickness of the layer of uniform thickness after removal of the external force is substantially the same as of the layer of uniform thickness before removing the conformable pressing force. In some embodiments, after removal of the external force, the thickness of the layer of uniform thickness deviates from the spacer height by a number equal to or less than 50%, 40%, 30%, 20%, 10%, 8%, 5%, 2.5%, 1%, 0.75%, 0.5%, 0.25%, 0.1%, or 0. In some embodiments, after removal of the conformable pressing force, the thickness of the layer of uniform thickness deviates from the spacer height by less than 10%.

B-2. Methods of Sample Analysis Using QMAX Device with Different Spacer Heights

Another aspect of the present invention provides a method using the QMAX device for analyzing a sample. In some embodiments, the method comprises the steps of:

(a) obtaining a sample suspected of containing a target analyte;

(b) obtaining a first, a second plates, and spacers, wherein:

vi. the plates are movable relative to each other into different configurations, including an open configuration and a closed configuration;

vii. one or both of the plates are flexible;

viii. the first plate has, on its inner surface, a first and a second sample contact area at different locations, and the second plate has, on its inner surface, a first and a second sample contact area at different locations that are corresponding to the first and the second sample contact areas of the first plate, respectively, wherein the sample contact areas are for contacting the sample;

ix. the spacers are fixed to the respective inner surface of one or both of the plates and have a predetermined substantially uniform height in each sample contact area; and x. the height of the spacers in the first sample contact area is different from that in the second sample contact area;

(c) depositing the sample on one or both of the plates when the plates are in the open configuration, wherein the open configuration is a configuration in which the two plates are partially or entirely separated apart, the spacing between the two plates is not regulated by the spacers, and the sample is deposited on one or both of the plates;

(d) after (c), bringing the two plates together and pressing the plates into the closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein the closed configuration is configured after the sample deposition in the open configuration, and in the closed configuration: the respectively corresponding sample contact areas are over one another, and at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area;

and (e) analyzing the target analyte in the layer of uniform thickness when the plates are in the closed configuration.

In some embodiments, the analyzing step comprises performing an assay in the layer of uniform thickness. The term "assaying" refers to testing a sample to detect the presence and/or abundance of a target analyte. In some embodiments, the assay is a binding assay that detects a target analyte-related signal by specific binding of the target analyte with a labeled detection agent. In some embodiments, the assay is a biochemistry assay that detects a target analyte by specific labeling of the target analyte or the biochemical reaction products of the target analyte.

In some embodiments, the analyzing step comprises measuring a target analyte-related signal, such as, but not limited to, the target analyte-related signal generated in the assay described above. In some embodiments, the signal includes, but not limited to, luminescence such as photoluminescence, electroluminescence, and electrochemiluminescence, light absorption, light reflection, light transmission, light diffraction, light scattering, light diffusion; surface Raman scattering, electrical impedance such as resistance, capacitance, and inductance, magnetic relaxivity, and any combination thereof.

B-3. Volume Multiplexing

In some embodiments, the spacers having different heights are capable of adding a layer of multiplexing possibility to the sample analysis the QMAX device may be used for. This is due to the fact that in the layer of uniform thickness, the spacer height regulates the relevant volume of the sample to be analyzed, and therefore the amount of target analytes contained within the relevant volume. The term "relevant volume" refers to a part of or an entire volume of the sample. In some embodiments, in the layer of uniform thickness, the relevant volume of the sample can be determined by measuring the lateral area of the relevant sample volume and calculating the volume from the lateral area and the predetermined spacer height. Therefore, the relevant volume is proportional to the spacer height within a given lateral area of layer of uniform thickness. Consequentially, the amount of target analyte within each sample contact area is proportional to the spacer height. In some embodiments, the different spacer heights render the sample contact areas in contact with different amount of target analyte ("volume multiplexing").

In some embodiments, the QMAX device is used for an assay to analyze a liquid sample, and the sample contact area comprises a binding site and/or a storage site for the assay. The term "binding site" refers to a location on a solid surface that can immobilize an entity in a sample, and the term "storage site" refers to a site of an area on a plate, wherein the site contains reagents to be added into a sample, and the reagents are capable of being dissolving into the sample that is in contact with the reagents and diffusing in the sample.

In some embodiments, the QMAX device is especially suitable for parallel multiplexed assays of liquid sample, as described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

For multiplexing purposes, in some embodiments, the first plate has, one or a plurality of the sample contact areas, a binding site that has a predetermined area and contains a capture agent capable of binding and immobilizing the target analyte. In some embodiments, the second plate has, one or a plurality of the sample contact areas, a storage site that has a predetermined area and contains a detection agent of a concentration, that upon contacting the sample, dissolves into the sample and diffuses in the sample.

In some embodiments, the plurality of binding sites comprise capture agent of different species or same capture agent of different concentrations. In some embodiments, the plurality of storage sites comprise different detection agents of different species or same detection reagents of different concentrations. In some embodiments, in the closed configuration, the corresponding storage sites are over the binding sites respectively.

In some embodiments of the QMAX device, there is no fluidic isolation between the binding sites and/or the storage sites. In some embodiments, separation between edges of neighboring binding sites and/or neighboring storage sites is larger than the distance that a target analyte or detection agent can diffuse in a relevant time. The term "relevant time" as used herein refers to a time length that is: (i) about equal to or longer than the time that it takes for the target analyte to diffuse across the thickness of the uniform thickness layer at the closed configuration; and (ii) shorter than the time that it takes the target analyte to laterally diffuse across the linear dimension of the predetermined area of the binding site.

In some embodiments, the spacers having different heights are capable of adding another layer of multiplexing possibility to assay, as described above, using the QMAX device. That is on top of having a plurality of binding sites and/or storage sites that comprises different assay reagents (e.g., capture agents, detection agents) or same assay reagents with different concentrations, the QMAX device is capable of offering different sample volumes or different amounts of analyte for multiplexing purposes.

In some embodiments of the QMAX device with volume multiplexing, there is no fluidic isolation between neighboring sample contact areas, and separation between edges of neighboring sample contact areas is larger than the distance that a target analyte or detection agent can diffuse in a relevant time. Therefore, in these embodiments, each sample contact area comprises a unique combination of the spacer height, the binding site, and the storage site. A combination of three different parameters can be tested for an assay in parallel using the same QMAX device.

In some embodiments of the methods using the QMAX device, in order to realize the parallel multiplexed assay, the analyzing step (e) comprises:

(1) incubating the sample for a relevant time length and then stopping the incubation; or (2) incubating the sample for a time that is equal or longer than the minimum of a relevant time length, and then assessing, within a time period that is equal to or less than the maximum of the relevant length of time, the binding of each target analyte to a binding site, thereby producing a reaction in which, at the end of the incubation in (1) or during the assessing in (2), the majority of the target analyte in the capture agent-target analyte-detection agent sandwich bound to each binding site is from a corresponding relevant volume of the sample;

wherein the incubation allows each target analyte to bind to a binding site and a detection agent, wherein the corresponding relevant volume is a portion of the sample that is above the corresponding storage site at the closed configuration.

B-4. Assay Optimization and Quantification

In some embodiments, the volume multiplexing rendered by the different spacer heights is useful for assay optimization and obtaining an optimal analyte-related signal in a regular assay. In many cases, bio/chemical assays rely on detecting an analyte by specific reacting with, binding and/or labeling of the analyte with the addition of external assay reagents into the sample. Therefore, one major obstacle in optimizing these assays is to determine the appropriate amount of assay agents added to the sample, in order to obtain an optimal detectable signal that accurately reflects the genuine amount of the analyte in the sample. This usually requires, among many others, a number of factors to be considered:

1) the general amount of assay reagents relative to the potential amount of analyte in the sample. Generally speaking, relatively smaller amount of assay reagents would lead to the risk of undetectable signal, saturation by the analyte, etc.; on the other hand, largely excessive amount of assay reagents is often costly and unnecessary.

2) the relative amount of each assay reagent, such as, but not limited to, binding agent, detection agent, capture agent, primary antibody, secondary antibody, oligonucleotide probe, or staining dye. For instance, in the case of competitive immunoassay, the relative ratio of the two reciprocal binding agents, one of which binds to the analyte and competitively inhibits the binding between the two reciprocal binding agents, is critical for the assay. And often the relative amount of the analyte in the sample determines the optimal ratio of the two reciprocal binding agents, as recognized in the art. Inappropriate amount of either one of the two would lead to false or inaccurate results in regards to the amount of analyte.

3) the detection threshold of the detector as used for receiving and analyzing the analyte-related signal. Detectors usually have a minimum and a maximum detection threshold, defining the lower and upper limit of the strength of the signal, within the range of which the detector is capable of receiving and analyzing the analyte-related signal and giving out meaningful results in regards to the amount of the analyte in the sample.

Given the foregoing factors and many others, conventionally in the art, tedious experimentation for assay optimization that consumes many material resources is required for the development of a valid and optimal bio/chemical assay, and very often such an optimization step is hard to be implemented at the point of use with limited resources and time. In some embodiments of the present invention, the addition of the volume multiplexing by the use of different spacer heights in the QMAX device expands the possibility of testing different combinations of the assay reagents and the sample. In addition to having different amounts or species of assay reagents in different sample contact areas, one can use spacers of different heights to render different sample contact areas in contact with possibly different pre-determined volumes of the sample, and the target analyte-related signals generated therein would consequentially be different and proportional to the spacer heights therein.

In some embodiments, the addition of volume multiplexing renders it possible to obtain an optimal target analyte-related signal from a number of different target analyte-related signals obtained from different sample contact areas, for the analysis of the target analyte in the sample. In some embodiments, the optimal target analyte-related signal is the signal within the minimum and maximum detection thresholds of the detector. In some embodiments, the optimal target analyte-related signal is the signal that accurately reflects the amount of target analyte in the sample, for instance, within the linear detection range of the assay, as understood by skilled artisans in the field.

In some embodiments, the addition of volume multiplexing renders it possible to optimize the assay at the point of use. In some embodiments, the addition of volume multiplexing saves the assay reagents that are needed for optimization, due to the small volume of sample need for the use of QMAX device.

Another aspect of the present invention provides a method using the QMAX device for analyzing a sample. In some embodiments, the method comprises the steps of:

(a) obtaining a sample suspected of containing a target analyte (b) obtaining a first, a second plate, and spacers, wherein:
  i. the plates are movable relative to each other into different configurations, including an open configuration and a closed configuration;
  ii. one or both of the plates are flexible;
  iii. the first plate has, on its inner surface, a first and a second sample contact area at different locations, and the second plate has, on its inner surface, a first and a second sample contact area at different locations that are corresponding to the first and the second sample contact areas of the first plate, respectively, wherein the sample contact areas are for contacting the sample;
  iv. the spacers are fixed to the respective inner surface of one or both of the plates and have a predetermined substantially uniform height in each sample contact area; and
  v. the height of the spacers in the first sample contact area is different from that in the second sample contact area;

(c) depositing the sample on one or both of the plates when the plates are in the open configuration,
  wherein the open configuration is a configuration in which the two plates are partially or entirely separated apart, the spacing between the two plates is not regulated by the spacers, and the sample is deposited on one or both of the plates;

(d) after (c), bringing the two plates together and pressing the plates into the closed configuration,
  wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and
  wherein in the closed configuration: the respectively corresponding sample contact areas are over one another, and at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area; and (e) analyzing the presence or absence, quantity, and/or concentration of the target analyte in the layer of uniform thickness by: (1) measuring a target analyte-related signal in the layer over the first and the second sample contact areas, respectively; (2) determining a ratio of the signal measured over the first sample contact area versus that over the second sample contact area, wherein the target analyte-related signal is a signal that is proportional to and reflects the amount of the target analyte in the sample.

B-5. Examples of Present Invention

BA1. A device for analyzing a liquid sample, comprising:
  a first plate, a second plate, and spacers, wherein:
  vi. the plates are movable relative to each other into different configurations;
  vii. one or both plates are flexible;
  viii. the first plate has, on its inner surface, a first and a second sample contact areas at different locations, and the second plate has, on its inner surface, a first and a second sample contact areas at different locations that are corresponding to the first and the second sample contact areas of the first plate, respectively, wherein the sample contact areas are for contacting a sample suspected of containing a target analyte;
  ix. the spacers are fixed to the respective inner surface of one or both of the plates and have a predetermined substantially uniform height in each sample contact area; and
  x. the height of the spacers in the first sample contact area is different from that in the second sample contact area;
  wherein one of the configurations is an open configuration, in which: the two plates are partially or entirely separated apart, the spacing between the plates is not regulated by the spacers, and the sample is deposited on one or both of the plates; and
  wherein another of the configurations is a closed configuration, which is configured after the sample deposition in the open configuration, and in the closed configuration: the respectively corresponding sample contact areas are over one another, and at least part of the deposited sample is compressed by the two plates into a layer that is confined by the two plates and has a respective substantially uniform thickness over each of the sample contact areas, wherein the uniform thickness of the layer is confined by the respective sample contact area and is regulated by the plates and the spacers in the respective sample contact area.

BB1. A device for parallel multiplexed assay of a liquid sample, comprising:
  a first plate, a second plate, and spacers, wherein:
  i. the plates are movable relative to each other into different configurations;
  ii. one or both of the plates are flexible;
  iii. the first plate has, on its inner surface, a first and a second sample contact areas at different locations, and the second plate has, on its inner surface, a first and a second sample contact areas at different locations that are corresponding to the first and the second sample contact areas of the first plate, respectively, wherein the sample contact areas are for contacting a sample suspected of containing a target analyte;
  iv. the first plate has, on at least one of the sample contact areas, a binding site that has a predetermined lateral area and contains a capture agent capable of binding and immobilizing the target analyte;
  v. a first and a second sample contact areas the second plate has, on at least one of the sample contact areas, a storage site that has a predetermined lateral area and contains a detection agent, that upon contacting the sample, dissolves and diffuses in the sample;

vi. the spacers are fixed to the respective inner surface of one or more of the plates and have a predetermined substantially uniform height in each sample contact area; and vii. the height of the spacers in the first sample contact area is different from that in the second sample contact area;

wherein one of the configurations is an open configuration, in which: the two plates are partially or entirely separated apart, the spacing between the plates is not regulated by the spacers, and the sample is deposited on one or both of the plates;

wherein another of the configurations is a closed configuration, which is configured after the sample deposition in the open configuration, and in the closed configuration: the respectively corresponding sample contact areas on the two plates are over one another; and at least part of the deposited sample is compressed by the two plates into a layer that is confined by the two plates and has a respective substantially uniform thickness over each of the sample contact areas, wherein the uniform thickness of the layer is confined by the respective sample contact area and is regulated by the plates and the spacers in the respective sample contact area;

wherein each capture agent, target analyte and corresponding detection agent are capable of forming a capture agent-target analyte-detection agent sandwich in the binding site of the first plate;

wherein there is no fluidic isolation between neighboring sample contact areas; and wherein a smallest separation between edges of neighboring sample contact areas is substantially larger than the distance that a target analyte or detection agent can diffuse in a time period that is:

(1) about equal to or longer than the time that it takes for the target analyte to diffuse across the thickness of the uniform thickness layer at the closed configuration; and (2) shorter than the time that it takes for the target analyte to laterally diffuse across the linear dimension of the predetermined area of the binding site.

BC1. A method for analyzing a liquid sample, comprising the steps of:

(a) obtaining a sample suspected of containing a target analyte;

(b) obtaining a first, a second plates, and spacers, wherein:

xi. the plates are movable relative to each other into different configurations, including an open configuration and a closed configuration;

xii. one or both of the plates are flexible;

xiii. the first plate has, on its inner surface, a first and a second sample contact area at different locations, and the second plate has, on its inner surface, a first and a second sample contact areas at different locations that are corresponding to the first and the second sample contact areas of the first plate, respectively, wherein the sample contact areas are for contacting the sample;

xiv. the spacers are fixed to the respective inner surface of one or both of the plates and have a predetermined substantially uniform height in each sample contact area; and xv. the height of the spacers in the first sample contact area is different from that in the second sample contact area;

(c) depositing the sample on one or both of the plates when the plates are in the open configuration, wherein the open configuration is a configuration in which the two plates are partially or entirely separated apart, the spacing between the two plates is not regulated by the spacers, and the sample is deposited on one or both of the plates;

(d) after (c), bringing the two plates together and pressing the plates into the closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein the closed configuration is configured after the sample deposition in the open configuration, and in the closed configuration: the respectively corresponding sample contact areas are over one another, and at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area;

and (e) analyzing the target analyte in the layer of uniform thickness when the plates are in the closed configuration.

BCC1. A method for analyzing a liquid sample, comprising the steps of:

(a) obtaining a sample suspected of containing a target analyte (b) obtaining a first, a second plate, and spacers, wherein:

vi. the plates are movable relative to each other into different configurations, including an open configuration and a closed configuration;

vii. one or both of the plates are flexible;

viii. the first plate has, on its inner surface, a first and a second sample contact area at different locations, and the second plate has, on its inner surface, a first and a second sample contact areas at different locations that are corresponding to the first and the second sample contact areas of the first plate, respectively, wherein the sample contact areas are for contacting the sample;

ix. the spacers are fixed to the respective inner surface of one or both of the plates and have a predetermined substantially uniform height in each sample contact area; and x. the height of the spacers in the first sample contact area is different from that in the second sample contact area;

(c) depositing the sample on one or both of the plates when the plates are in the open configuration, wherein the open configuration is a configuration in which the two plates are partially or entirely separated apart, the spacing between the two plates is not regulated by the spacers, and the sample is deposited on one or both of the plates;

(d) after (c), bringing the two plates together and pressing the plates into the closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein in the closed configuration: the respectively corresponding sample contact areas are over one another, and at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area; and (e) analyzing the presence or absence, quantity, and/or concentration of the target analyte in the layer of uniform thickness by: (1) measuring a target analyte-related signal in the layer over the first and the second sample contact areas, respectively; (2) determining a ratio of the signal measured over the first sample contact area versus that over the second sample contact area, wherein the target analyte-related signal is a signal that is proportional to and reflects the amount of the target analyte in the sample.

BD1. A method for a parallel multiplexed assay of a liquid sample, comprising the steps of:

(a) obtaining a sample suspected of containing a target analyte (b) obtaining a first plate, a second plate, and spacers, wherein:

viii. the plates are movable relative to each other into different configurations, including an open configuration and a closed configuration;

ix. one or both of the plates are flexible;

x. the first plate has, on its inner surface, a first and a second sample contact areas at different locations, and the second plate has, on its inner surface, a first and a second sample contact areas at different locations that are corresponding to the first and the second sample contact areas of the first plate, respectively, wherein the sample contact areas are for contacting the sample;

xi. the first plate has, on at least one of the sample contact areas, a binding site that has a predetermined lateral area and contains a capture agent capable of binding and immobilizing the target analyte;

xii. a first and a second sample contact areas the second plate has, on at least one of the sample contact areas, a storage site that has a predetermined lateral area and contains a detection agent, that upon contacting the sample, dissolves and diffuses in the sample; and xiii. the spacers are fixed to the respective inner surface of one or both of the plates and have a predetermined substantially uniform height in each sample contact area; and wherein each capture agent, target analyte and corresponding detection agent are capable of forming a capture agent-target analyte-detection agent sandwich in a binding site of the first plate;

(c) depositing the sample on one or both of the plates when the plates are in the open configuration, wherein the open configuration is a configuration in which the two plates are partially or entirely separated apart, the spacing between the plates is not regulated by the spacers, and the sample is deposited on one or both of the plates;

(d) after (c), bringing the two plates together and pressing the plates into the closed configuration, wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and wherein the closed configuration is configured after the sample deposition at the open configuration, and in the closed configuration: the corresponding sample contact areas on the two plates are over one another, respectively; and at least part of the deposited sample is compressed by the two plates into a layer that is confined by the two plates and has a respective substantial uniform thickness over each of the sample contact areas, wherein the uniform thickness of the layer is confined by the respective sample contact area of the plates and is regulated by the plates and the spacers in the respective sample contact area; and (e) after (d) and while the plates are in the closed configuration:

(1) incubating the sample for a relevant time length and then stopping the incubation; or (2) incubating the sample for a time that is equal or longer than the minimum of a relevant time length, and then assessing, within a time period that is equal to or less than the maximum of the relevant length of time, the binding of each target analyte to a binding site, thereby producing a reaction in which, at the end of the incubation in (1) or during the assessing in (2), the majority of the target analyte in the capture agent-target analyte-detection agent sandwich bound to each binding site is from a corresponding relevant volume of the sample;

wherein the incubation allows each target analyte to bind to a binding site and a detection agent, wherein the corresponding relevant volume is a portion of the sample that is above the corresponding storage site at the closed configuration, and wherein the relevant time is:

(i) about equal to or longer than the time that it takes for the target analyte to diffuse across the thickness of the uniform thickness layer at the closed configuration; and (ii) shorter than the time that it takes for the target analyte to laterally diffuse across the linear dimension of the predetermined area of the binding site.

BA2. The device of embodiment BA1, wherein the uniform heights of the spacers are in the range of 0.5 to 100 μm.

BA3. The device of any one of prior embodiments, wherein the uniform heights of the spacers are in the range of 0.5 to 20 μm.

BA4. The device of any one of prior embodiments, wherein the difference between the uniform heights of the spacers in the first and second sample contact areas is in the range of 0.5 to 100 □m.

BA5. The device of any one of prior embodiments, wherein the difference between the uniform heights of the spacers in the first and second sample contact areas is in the range of 0.5 to 50 □m.

BA6. The device of any one of prior embodiments, wherein the spacers have a predetermined substantially constant inter-spacer distance in each sample contact area;

BA7. The device of embodiment BA6, wherein the constant inter-spacer distances of the spacers are in the range of 7 to 200 □m.

BA8. The device of embodiment BA6, wherein the constant inter-spacer distances of the spacers are in the range of 50 to 150 □m.

BA9. The device of any one of prior embodiments, wherein a separation between edges of neighboring sample contact areas is in the range of 20 □m to 1 mm.

BA10. The device of any one of prior embodiments, wherein a separation between edges of neighboring sample contact areas is in the range of 100 to 500 □m.

BA11. The device of any one of prior embodiments, wherein an average value of the uniform thickness of the layer in each sample contact area is substantially the same as the uniform height of the spacers therein with a variation of less than 10%.

BA12. The device of any one of prior embodiments, wherein the first plate has, on at least one of the sample contact areas, a binding site that has a predetermined lateral area and contains a capture agent capable of binding and immobilizing the target analyte.

BA13. The device of embodiment BA12, wherein in the closed configuration, the uniform thickness of the layer in any one of the sample contact areas is substantially less than the predetermined lateral area of the binding site therein.

BA14. The device of any one of prior embodiments, wherein the second plate has a first and a second sample contact areas at different locations that are corresponding to the first and the second sample contact areas of the first plate, respectively, wherein the respectively corresponding sample contact areas are over one another in the closed configuration.

BA15. The device of embodiment BA14, wherein the second plate has, on at least one of the sample contact areas, a storage site that has a predetermined lateral area and contains a detection agent, that upon contacting the sample, dissolves and diffuses in the sample.

BA16. The device of any one of prior embodiments, wherein a smallest separation between edges of neighboring sample contact areas is substantially larger than the distance that a target analyte or detection agent can diffuse in a relevant time, wherein the relevant time is:
  iii. about equal to or longer than the time that it takes for the target analyte to diffuse across the thickness of the uniform thickness layer at the closed configuration; and
  iv. shorter than the time that it takes for the target analyte to laterally diffuse across the linear dimension of the predetermined area of the binding site.

BA17. The device of any one of prior embodiments, wherein there is no fluidic isolation between neighboring sample contact areas.

BC2. The method of any one of embodiment BC1 or BCC1, wherein the uniform heights of the spacers are in the range of 0.5 to 100 μm.

BC3. The method of any one of prior method embodiments, wherein the uniform heights of the spacers are in the range of 0.5 to 20 μm.

BC4. The method of any one of prior method embodiments, wherein the difference between the uniform heights of the spacers in the different sample contact areas is in the range of 0.5 to 100 □m.

BC5. The method of any one of prior method embodiments, wherein the difference between the uniform heights of the spacers in the different sample contact areas is in the range of 0.5 to 50 □m.

BC6. The method of any one of prior method embodiments, wherein the spacers have a predetermined substantially constant inter-spacer distance in each sample contact area;

BC7. The method of embodiment BC6, wherein the constant inter-spacer distances of the spacers are in the range of 7 to 200 □m.

BC8. The method of embodiment BC6, wherein the constant inter-spacer distances of the spacers are in the range of 50 to 150 □m.

BC9. The method of any one of prior method embodiments, wherein a separation between edges of neighboring sample contact areas is in the range of 20 ⊐m to 1 mm.

BC10. The method of any one of prior method embodiments, wherein a separation between edges of neighboring sample contact areas is in the range of 100 to 500 □m.

BC11. The method of any one of prior method embodiments, wherein an average value of the uniform thickness of the layer in each sample contact area is substantially the same as the uniform height of the spacers therein with a variation of less than 10%.

BC12. The method of any one of prior method embodiments, further comprising: after step (d) and before step (e), removing the conformable pressing force, wherein the thickness of the layer of uniform thickness after removal of the conformable pressing force: (i) is substantially the same as of the layer of uniform thickness before removing the conformable pressing force and (ii) deviates from the spacer height by less than 10%.

BC13. The method of any one of prior method embodiments, wherein the conformable pressing is performed by human hand.

BC14. The method of any one or prior method embodiments, wherein the conformable pressing is provided by a pressured liquid, a pressured gas, or a conformable material.

BC15. The method of any one of prior method embodiments, wherein the sample deposition of step (c) is a deposition directly from a subject to the plate without using any transferring devices.

BC16. The method of any one of prior method embodiments, wherein during the deposition of step (c), the amount of the sample deposited on the plate is unknown.

BC17. The method of any one or prior method embodiments, wherein the analyzing in step (e) comprises performing an assay in the layer of uniform thickness.

BC18. The method of embodiment BC17, wherein the assay is a binding assay or biochemistry assay.

BC19. The method of any one of prior method embodiments, wherein the first plate has, on at least one of the sample contact areas, a binding site that has a predetermined lateral area and contains a capture agent capable of binding and immobilizing the target analyte.

BC20. The method of embodiment BC19, wherein in the closed configuration, the uniform thickness of the layer in any one of the sample contact areas is substantially less than the predetermined lateral area of the binding site therein.

BC21. The method of any one of prior method embodiments, wherein the second plate has, on at least one of the sample contact areas, a storage site that has a predetermined lateral area and contains a detection agent of a concentration, that upon contacting the sample, dissolves into the sample and diffuses in the sample.

BC22. The method of any one of prior method embodiments, wherein a smallest separation between the edges of neighboring sample contact areas is substantially larger than the distance that a target analyte or detection agent can diffuse in a relevant time, wherein there is no fluidic isolation between the neighboring sample contact areas, wherein the relevant time length is:

iii. about equal to or longer than the time that it takes for the target analyte to diffuse across the thickness of the uniform thickness layer at the closed configuration; and
iv. shorter than the time that it takes the target analyte to laterally diffuse across the linear dimension of the predetermined area of the binding site.

BC23. The method of any one of prior method embodiments, wherein the analyzing of step (e) comprises:
(1) incubating the sample for a relevant time length and then stopping the incubation; or
(2) incubating the sample for a time that is equal or longer than the minimum of a relevant time length, and then assessing, within a time period that is equal to or less than the maximum of the relevant length of time, the binding of each target analyte to a binding site, thereby producing a reaction in which, at the end of the incubation in (1) or during the assessing in (2), the majority of the target analyte in the capture agent-target analyte-detection agent sandwich bound to each binding site is from a corresponding relevant volume of the sample;

wherein the incubation allows each target analyte to bind to a binding site and a detection agent, wherein the corresponding relevant volume is a portion of the sample that is above the corresponding storage site at the closed configuration.

BC24. The method of any one of prior method embodiments, wherein the reaction is saturated in less than 60 seconds.

BC25. The method of any one or prior method embodiments, wherein the relevant time length is in the range of 60 seconds to 30 minutes.

BC26. The method of any one of prior method embodiments, wherein the analyzing in step (e) comprises measuring a target analyte-related signal selected from the group consisting of:
vii. luminescence selected from photoluminescence, electroluminescence, and electrochemiluminescence;
viii. light absorption, reflection, transmission, diffraction, scattering, or diffusion;
ix. surface Raman scattering;
x. electrical impedance selected from resistance, capacitance, and inductance;
xi. magnetic relaxivity; and
xii. any combination of i-v,
wherein the target analyte-related signal is a signal that is proportional to and reflects the amount of the target analyte in the sample.

BC27. The method of embodiment BC26, wherein the analyzing step (e) comprises:
determining an optimal signal from the target analyte-related signals measured from relevant sample contact areas, wherein the relevant sample contact areas are the sample contact areas that contain the binding site and/or storage site for detecting the same target analyte.

BC28. The method of embodiment BC26, wherein the optimal target analyte-related signal is determined by selecting the measured target analyte-related signal within a range between minimum and maximum detection thresholds, wherein the minimum and maximum detection thresholds of the plates and a detector used for the signal measuring.

BC29. The method of embodiment BC26, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

BC30. The method of any one of prior method embodiments, wherein the analyzing step (e) comprises calculating the volume of a relevant sample volume by measuring the lateral area of the relevant sample volume and calculating the volume from the lateral area and the predetermined spacer height, wherein the relevant volume is a part of or an entire volume of the sample.

BC31. The method of any one of prior method embodiments, wherein the analyzing step (e) comprises reading, image analysis, or counting of the target analyte, or a combination of thereof.

BC32. The method of any one of prior method embodiments, further comprising one or more washes.

BC33. The method of any one of prior method embodiments, wherein the deposited sample has a total volume less 0.5 ⌐L.

BC34. The method of any one of prior method embodiments, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

BC35. The method of any one of prior method embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

BC36. The method of any one of prior method embodiments, wherein the sample is an environmental gaseous sample from a source selected from the group consisting of: the air, underwater heat vents, industrial exhaust, vehicular exhaust, and any combination thereof.

BC37. The method of any one of prior method embodiments, wherein the sample is a foodstuff sample selected from the group consisting of: raw ingredients, cooked food, plant and animal sources of food, preprocessed food, and partially or fully processed food, and any combination thereof.

BC38. The method of any one of prior method embodiments, wherein the sample is human blood, and the depositing step comprises: (a) pricking the skin of a human release a droplet of blood onto the skin; and (b) contacting the droplet of blood with the filter without use of a blood transfer tool.

BD2. The method of embodiment BD1, wherein step (e) comprises measuring a target analyte-related signal selected from the group consisting of:
vii. luminescence selected from photoluminescence, electroluminescence, and electrochemiluminescence;
viii. light absorption, reflection, transmission, diffraction, scattering, or diffusion;
ix. surface Raman scattering;
x. electrical impedance selected from resistance, capacitance, and inductance;
xi. magnetic relaxivity; and
xii. any combination of i-v, wherein the target analyte-related signal is a signal that is proportional to and reflects the binding of target analyte to the binding site.

BD3. The method of embodiment BD2, wherein the analyzing step (e) comprises:
determining an optimal signal from the target analyte-related signals measured from relevant sample contact areas, wherein the relevant sample contact areas are the sample contact areas that contain the binding site and/or storage site for detecting the same target analyte.

BD4. The method of embodiment BD3, wherein the optimal target analyte-related signal is determined by selecting the measured target analyte-related signal within a range between minimum and maximum detection thresholds, wherein the minimum and maximum detection thresholds of the plates and a detector used for the signal measuring.

BD5. The method of embodiment BD3, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

E23. The device or method of any one of prior embodiments, wherein the binding site is defined by a patch of dried reagent.

E24. The device or method of any one of prior embodiments, wherein the binding site is between a pair of electrodes.

E25. The device or method of any one of prior embodiments, wherein one or both plate inner surfaces comprise one or a plurality of amplification sites that are each capable of amplifying the target analyte-related signal when the target analyte is within 500 nm from an amplification site.

E26. The device or method of any one of prior embodiments, wherein the plates have a thickness of less than 200 μm.

E27. The device or method of any one of prior embodiments, wherein the plates have a thickness of less than 100 μm.

E28. The device or method of any one of prior embodiments, wherein each of the plates has an area of less than 5 cm².

E29. The device or method of any one of prior embodiments, wherein each of the plates has an area of less than 2 cm².

E30. The device or method of any one of prior embodiments, wherein at least one of the plates is partially or entirely transparent.

E31. The device or method of any one of prior embodiments, wherein at least one of the plates is made from a flexible polymer.

E32. The device or method of any one of prior embodiments, wherein at least one of the plates is a flexible plate, and the thickness of the flexible plate times the Young's modulus of the flexible plate is in the range of 60 to 75 GPa-μm.

E33. The device or method of any one of prior embodiments, wherein the spacers are spacers with a cross sectional shape selected from round, polygonal, circular, square, rectangular, oval, elliptical, or any combination of the same.

E34. The device or method of any one of prior embodiments, wherein the spacers have a pillar shape and a substantially flat top surface, wherein, for each spacer, the ratio of the lateral dimension of the spacer to its height is at least 1.

E35. The device or method of any one of prior embodiments, wherein each spacer has the ratio of the lateral dimension of the spacer to its height is at least 1.

E36. The device or method of any one of prior embodiments, wherein the minimum lateral dimension of spacer is less than or substantially equal to the minimum dimension of a target analyte in the sample.

E37. The device or method of any one of prior embodiments, wherein the spacers have a pillar shape, and the sidewall corners of the spacers have a round shape with a radius of curvature at least 1 μm.

E38. The device or method of any one of prior embodiments, wherein the spacers have a density of at least 100/mm².

E39. The device or method of any one of prior embodiments, wherein the spacers have a density of at least 1000/mm².

E40. The device or method of any one of prior embodiments, wherein the spacers have a filling factor of at least 1%, wherein the filling factor is the ratio of the spacer area in contact with the layer of uniform thickness to the total plate area in contact with the layer of uniform thickness.

E41. The device or method of any one of prior embodiments, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

E42. The device or method of any one of prior embodiments, wherein
a. at least one of the plates is flexible, and
b. for the flexible plate, the fourth power of the inter-spacer-distance (ISD) divided by the thickness of the flexible plate (h) and the Young's modulus (E) of the flexible plate, $ISD^4/(hE)$, is equal to or less than 106 um³/GPa.

E43. The device or method of any one of prior embodiments, wherein the spacers are fixed on a plate by directly embossing the plate or injection molding of the plate.

E44. The device or method of any one of prior embodiments, wherein the materials of the plate and the spacers are independently selected from polystyrene, PMMG, PC, COC, COP, or another plastic.

C. SELECTIVE LYSING (066)

In some embodiments, the devices and methods provided by the present invention are capable of lysing a target percentage of a component in a liquid sample. In some embodiments, each of the plates has, on its respective sample surface, a sample contact area for contacting a sample, wherein the sample comprises at least a target lysing component. In some embodiments, at least one parameter of the pillars is selected such that, during a process of the plates transitioning from the open configuration to the closed configuration, a target percentage of the target lysing component of the sample in the relevant volume is lysed by the pillars.

In some embodiments, the target percentage is 5% or less, 10% or less, 20% or less, 30% or less, 40% or less, 50% or less, 60% or less, 70% or less, 80% or less, 90% or less, 95% or less, 98% or less, 99% or less, 100% or less, or any value in a range between any two of these numbers.

Yet another aspect of the present invention provides devices and methods that can effectively and rapidly perform mechanical lysis of select cell types in a given sample while preserving other types of cells in the sample.

In some embodiments, the devices and methods are used for selectively lysing a component in a liquid sample. In some embodiments, each of the plates has, on its respective sample surface, a sample contact area for contacting a sample, wherein the sample comprises at least a target lysing component and at least a non-target lysing component. In some embodiments, at least one parameter of the pillars is selected such that, during a process of the plates transitioning from the open configuration to the closed configuration, a substantial fraction of the target lysing component of the sample in the relevant volume is lysed by the pillars, and a substantial fraction of the non-target lysing component in the relevant volume is not lysed.

In some embodiments, the devices and methods are capable of selectively lysing a target lysing component in one part of a liquid sample, while leaving the target lysing component unlysed in another part of the sample. In some embodiments, the first plate has, on its respective sample surface, a first sample contact area at one location and a second sample contact area at another location, wherein the sample contact areas are for contacting a sample, and wherein the sample comprises at least a target lysing component. In some embodiments, in the open configuration: the two plates are partially or completely separated apart and the spacing between the plates is not regulated by the pillars, and the sample is deposited on one or both of the plates. In some embodiments, in the closed configuration: a relevant volume of the sample is compressed by the two plates into a layer of highly uniform thickness, and the uniform thickness of the layer is confined by the sample contact areas of the plates and is regulated by the plates and the pillars. In some embodiments, at least one parameter of the pillars is selected such that, (a) the pillars have substantially same the at least one parameter in the first sample contact area and a different substantially same the at least one parameter in in the second sample contact area, and (b) during a process of the plates transitioning from the open configuration to the closed configuration, a substantial fraction of the target-lysing component of the sample over the first sample contact area is lysed by the pillars, while the target lysing component is not lysed over the second sample contact area.

In some embodiments, the substantial fraction is 50% or more, 55% or more, 60% or more, 65% or more, 70% or more, 75% or more, 80% or more, 85% or more, 90% or more, 95% or more, 98% or more, 99% or more, 100%, or any value in a range between any two of these values.

In some embodiments, at least one of the plates is flexible. In some embodiments, the flexibility of the plate(s) results in that, when the two plates are compressed from an open configuration to enter a closed configuration, the local spacing between the two plates is regulated by the local pillar height, and the compressing force applied to the biological cells in the sample is regulated by the parameters of the local pillars.

In some embodiments, the at least one parameter of the pillars includes, but not limited to, the size, shape, material of the pillars, the top surface dimension of the pillars, and the alignment pattern (e.g. periodicity and density) of the pillar array.

5. Compressing Force

In the present invention, a force is used to compress the two plates to bring the plates from an open configuration to a closed configuration, and to help rupture the enclosure of the target lysing component.

In the present invention, the compressing forces include, but not limited to, mechanical force, electrostatic force, electromagnetic force (including the light), and any combination of thereof.

In some embodiments of bringing the plates from an open configuration to a closed configuration, an external force is applied to push the first plate and the second plate toward each other. In some embodiments, the external force is applied by a human hand.

In some embodiments of bring the plates from an open configuration to a closed configuration, an external pressure is applied to outside the first plate and the second plate to push the plates toward each other, and the pressure is higher than the pressure inside of the plate. A device is used to make the pressure of outside the plates higher than that inside the plate. The device includes, in limited to, a sealing device.

In certain embodiments, the compressing force (hence the sample deformation) is created by isolating the pressure between the first plate and the second plate (inside pressure) from that outside of the plates (outside pressure), and then make the inside pressure lower than the outside pressure. The isolation can be done using a vacuum seal or other devices.

In some embodiments, it is a combination of the methods described above.

In certain embodiments, the compressing force is applied in a process, termed "gradual pressing", which comprises: pressure (i.e. applying the compressing the force) is applied at one location of the plate(s) first, then gradually to other locations of the sample.

In one embodiment of the gradual pressing, a roller is used to press the first plate and the second plate (the sample is between the plates, and the plates are slightly flexible) against another roller or a flat surface.

In another embodiment, the human fingers are the tool of the pressing the plates (hence the sample). The pressing is one part of human hand against another part of human body (including another part of human hand) or a human hand against an object (e.g. a table surface).

In one embodiment of the gradual pressing, a pressed air jet is first directed to a location (e.g. the center) of the plate pair (which is between the first plate and the second plate, one of the plates is slightly flexible) and the pressure is gradually extended to other part of the plate pair.

In the present invention, the devices for applying the compressing force(s) for mechanical lysis have several implementations. Some embodiments are to use human hand to press, for example, to press by human fingers. Some embodiments are to use a pressing device, where the pressing device includes, but not limited to, a human hand(s), a mechanical clip, a mechanical press, mechanical clamp, a mechanical slider, a mechanical device, electromagnetic device, roller that rolls on a surface, two rollers against each other, fluidic press, a hydraulic device, or any combination of thereof. Certain embodiments are to use pressured liquid or pressured air to press the first plate and/or the second plate directly or indirectly. "Directly" means the pressured liquid or air is applied directly on the first plate and/or the second plate; and the "indirectly" means it is applied through a third object. Certain embodiments in pressing use a combination of the above embodiments of pressing devices and methods.

In some embodiments, the compressing force is applied for a period of time and then the two plates are released.

In some embodiments, the necessary compressing time may be established based on empirical evidence, in order to have a certain percentage of target lysing component lysed.

In some preferred embodiments, a significant characteristic of the lysing method provided in the present invention is that the time needed to compress the plates and hence lyse the target lysing component can be very short. In some preferred embodiments, the time needed to compress the plates may be only a few seconds.

In some embodiments, the two plates are compressed for a period of time and then released, but are self-held even after the external compressing force is eliminated, because of the forces still existing between the inner surfaces of the two plates, like capillary force.

In some embodiments, the two plates are compressed by external force for a period of time, including time for additional procedures other than the mere lysing process.

Examples of Present Invention

A1. A device for lysing a component in a liquid sample, comprising:
  a first plate and a second plate, wherein:
  i. the two plates are relatively movable to each other to enter different configurations, including an open configuration and a closed configuration,
  ii. each of the plates has, on its respective sample surface, a sample contact area for contacting a sample, wherein the sample comprises at least a target lysing component,
  iii. one or both of the plates comprise pillars that are fixed to the respective sample contact area, and
  iv. the pillars have at least one of lateral dimensions of pillar top surface being less than 200% of the target lysing component,
  wherein in the open configuration, the two plates are partially or completely separated apart and the spacing between the plates is not regulated by the pillars, and the sample is deposited on one or both of the plates;
  wherein the closed configuration is configured after deposition of the sample in the open configuration, and in the closed configuration: a relevant volume of the sample is compressed by the two plates into a layer of highly uniform thickness, and the uniform thickness of the layer is confined by the sample contact areas of the plates and is regulated by the plates and the pillars;
  wherein during a process of the plates transitioning from the open configuration to the closed configuration, a substantial fraction of the target lysing component of the sample in the relevant volume is lysed by the pillars; and
  wherein the relevant volume of the sample is a partial or entire volume of the sample.

A'-1. A method of mechanically lysing a component in a liquid sample, comprising the steps of:
  (a) having a first plate and a second plate, wherein:
    i. the two plates are relatively movable to each other to enter different configurations, including an open configuration and a closed configuration,
    ii. each of the plates has, on its respective sample surface, a sample contact area for contacting a sample, wherein the sample comprises at least a target lysing component,
    iii. one or both of the plates comprise pillars that are fixed to the respective sample contact area, and
    iv. the pillars have at least one of lateral dimensions of pillar top surface being less than 200% of the target lysing component,
  (b) depositing the sample on one or both of the plates when the plates are in the open configuration, wherein in the open configuration: the two plates are partially or completely separated apart and the spacing between the plates is not regulated by the pillars; and
  (c) bringing the two plates together, and compressing the two plates against each other with a force to enter the closed configuration, during which, a substantial fraction of the target lysing component of the sample in a relevant volume of the sample is lysed by the pillars;
    wherein in the closed configuration: the relevant volume of the sample is compressed by the two plates into a layer of highly uniform thickness, and the uniform thickness of the layer is confined by the sample contact areas of the plates and is regulated by the plates and the pillars, and
    wherein the relevant volume of the sample is a partial or entire volume of the sample.

B1. A device for selectively lysing a target percentage of a component in a liquid sample, comprising:
  a first plate and a second plate, wherein:
  i. the two plates are relatively movable to each other to enter different configurations, including an open configuration and a closed configuration,
  ii. each of the plates has, on its respective sample surface, a sample contact area for contacting a sample, wherein the sample comprises at least a target lysing component, and
  iii. one or both of the plates comprise pillars that are fixed to the respective sample contact area,
  wherein in the open configuration, the two plates are partially or completely separated apart and the spacing between the plates is not regulated by the pillars, and the sample is deposited on one or both of the plates;
  wherein the closed configuration is configured after deposition of the sample in the open configuration, and in the closed configuration: a relevant volume of the sample is compressed by the two plates into a layer of highly uniform thickness, and the uniform thickness of the layer is confined by the sample contact areas of the plates and is regulated by the plates and the pillars;
  wherein at least one parameter of the pillars is selected such that, during a process of the plates transitioning from the open configuration to the closed configuration, a target percentage of the target lysing component of the sample in the relevant volume is lysed by the pillars; and
  wherein the relevant volume of the sample is a partial or entire volume of the sample.

B'-1. A method of selectively lysing a target percentage of a component in a liquid sample, comprising the steps of:
  (a) having a first plate and a second plate, wherein:
    i. the two plates are relatively movable to each other to enter different configurations, including an open configuration and a closed configuration,
    ii. each of the plates has, on its respective sample surface, a sample contact area for contacting a sample, wherein the sample comprises at least a target lysing component, and
    iii. one or both of the plates comprise pillars that are fixed to the respective sample contact area,
  (b) depositing the sample on one or both of the plates when the plates are in the open configuration, wherein in the open configuration, the two plates are partially or completely separated apart and the spacing between the plates is not regulated by the pillars; and
  (c) bringing the two plates together, and compressing the two plates against each other with a force to enter the closed configuration,
    wherein in the closed configuration, a relevant volume of the sample is compressed by the two plates into a layer of highly uniform thickness, and the uniform thickness of the layer is confined by the sample contact areas of the plates and is regulated by the plates and the pillars,
    wherein at least one parameter of the pillars is selected such that, during a process of the plates transitioning from the open configuration to the closed configuration, a target percentage of the target lysing component of the sample in the relevant volume is lysed by the pillars, and wherein the relevant volume of the sample is a partial or entire volume of the sample.

C1. A device for selectively lysing a component in a liquid sample, comprising:
 a first plate and a second plate, wherein:
   i. the two plates are relatively movable to each other to enter different configurations, including an open configuration and a closed configuration,
   ii. each of the plates has, on its respective sample surface, a sample contact area for contacting a sample, wherein the sample comprises at least a target lysing component and at least a non-target lysing component, and
   iii. one or both of the plates comprise pillars that are fixed to the respective sample contact area,
 wherein in the open configuration, the two plates are partially or completely separated apart and the spacing between the plates is not regulated by the pillars, and the sample is deposited on one or both of the plates;
 wherein the closed configuration is configured after deposition of the sample in the open configuration, and in the closed configuration: a relevant volume of the sample is compressed by the two plates into a layer of highly uniform thickness, and the uniform thickness of the layer is confined by the sample contact areas of the plates and is regulated by the plates and the pillars;
 wherein at least one parameter of the pillars is selected such that, during a process of the plates transitioning from the open configuration to the closed configuration, a substantial fraction of the target lysing component of the sample in the relevant volume is lysed by the pillars, and a substantial fraction of the non-target lysing component in the relevant volume is not lysed; and
 wherein the relevant volume of the sample is a partial or entire volume of the sample.

C'-1. A method of selectively lysing a component in a liquid sample, comprising the steps of:
 (a) having a first plate and a second plate, wherein:
   i. the two plates are relatively movable to each other to enter different configurations, including an open configuration and a closed configuration,
   ii. each of the plates has, on its respective sample surface, a sample contact area for contacting a sample, wherein the sample comprises at least a target lysing component and at least a non-target lysing component, and
   iii. one or both of the plates comprise pillars that are fixed to the respective sample contact area,
 (b) depositing the sample on one or both of the plates when the plates are in the open configuration, wherein in the open configuration: the two plates are partially or completely separated apart and the spacing between the plates is not regulated by the pillars; and
 (c) bringing the two plates together, and compressing the two plates against each other with a force to enter the closed configuration,
   wherein in the closed configuration, a relevant volume of the sample is compressed by the two plates into a layer of highly uniform thickness, and the uniform thickness of the layer is confined by the sample contact areas of the plates and is regulated by the plates and the pillars,
   wherein at least one parameter of the pillars is selected such that, during a process of the plates transitioning from the open configuration to the closed configuration, a substantial fraction of the target lysing component of the sample in the relevant volume is lysed by the pillars, and a substantial fraction of the non-target lysing component in the relevant volume is not lysed, and
   wherein the relevant volume of the sample is a partial or entire volume of the sample.

D1. A device for selectively lysing a component in a liquid sample, comprising:
 a first plate and a second plate, wherein:
   i. the two plates are relatively movable to each other to enter different configurations, including an open configuration and a closed configuration,
   ii. the first plate has, on its respective sample surface, a first sample contact area at one location and a second sample contact area at another location, wherein the sample contact areas are for contacting a sample, wherein the sample comprises at least a target lysing component, and
   iii. one or both of the plates comprise pillars that are fixed to the respective sample contact area,
 wherein in the open configuration, the two plates are partially or completely separated apart and the spacing between the plates is not regulated by the pillars, and the sample is deposited on one or both of the plates;
 wherein the closed configuration is configured after deposition of the sample in the open configuration, and in the closed configuration: a relevant volume of the sample is compressed by the two plates into a layer of highly uniform thickness, and the uniform thickness of the layer is confined by the sample contact areas of the plates and is regulated by the plates and the pillars;
 wherein at least one parameter of the pillars is selected such that, (a) the pillars have substantially same the at least one parameter in the first sample contact area and a different substantially same the at least one parameter in in the second sample contact area, and (b) during a process of the plates transitioning from the open configuration to the closed configuration, a substantial fraction of the target-lysing component of the sample over the first sample contact area is lysed by the pillars, while the target lysing component is not lysed over the second sample contact area; and
 wherein the relevant volume of the sample is a partial or entire volume of the sample.

D'-1. A method of selectively lysing a component in a liquid sample, comprising the steps of:
 (a) having a first plate and a second plate, wherein:
   i. the two plates are relatively movable to each other to enter different configurations, including an open configuration and a closed configuration,
   ii. the first plate has, on its respective sample surface, a first sample contact area at one location and a second sample contact area at another location, wherein the sample contact areas are for contacting a sample, wherein the sample comprises at least a target lysing component, and
   iii. one or both of the plates comprise pillars that are fixed to the respective sample contact area,
 (b) depositing the sample on one or both of the plates when the plates are in the open configuration, wherein in the open configuration: the two plates are partially or completely separated apart and the spacing between the plates is not regulated by the pillars; and
 (c) bringing the two plates together, and compressing the two plates against each other with a force to enter the closed configuration,
   wherein in the closed configuration: a relevant volume of the sample is compressed by the two plates into a layer of highly uniform thickness, and the uniform thickness of the layer is confined by the sample contact areas of the plates and is regulated by the plates and the pillars, wherein at least one parameter of the pillars is selected such that, (a) the pillars have substantially same the at least one parameter in the first sample contact area and a different substantially same the at least one parameter in in the second sample contact area, and (b) during a process of the plates transitioning from the open configuration to the closed configuration, a substantial fraction of the target-lysing component of the sample over the first sample contact area is lysed by the pillars, while the target lysing component is not lysed over the second sample contact area, and wherein the relevant volume of the sample is a partial or entire volume of the sample.

F1. The device or method of any prior embodiment, wherein at least one of the plates is flexible.

F2. The device or method of any prior embodiment, wherein the base of at least one of the pillars has an approximate round shape.

F3. The device or method of any prior embodiment, wherein the base of at least one of the pillars has an approximate shape selected from the group consisting of polygonal, pyramidal, elliptical, and elongated bar shaped, and their combination thereof with round shape, and any combination thereof.

F4. The device or method of any prior embodiment, wherein the lateral dimension of the base of at least one of the pillars is 1 nm or less, 10 nm or less, 50 nm or less, 100 nm or less, 200 nm or less, 500 nm or less, 800 nm or less, 1000 nm or less, 2000 nm or less, 3000 nm or less, 5000 nm or less, 10 microns or less, 20 microns or less, 30 microns or less, 50 microns or less, 100 microns or less, 150 microns or less, 200 microns or less, 300 microns or less, 500 microns or less, 800 microns or less, 1 mm or less, 2 mm or less, 4 mm or less, or in a range between any two of the values.

F5. The device or method of any prior embodiment, wherein the top of at least one of the pillars has an approximate round shape.

F6. The device or method of any prior embodiment, wherein the top of at least one of the pillars has an approximate shape selected from the group consisting of polygonal, pyramidal, elliptical, and elongated bar shaped, and their combination with round shape, and any combination thereof.

F7. The device or method of any prior embodiment, wherein the lateral dimension of the top of at least one of the pillars is 1 nm or less, 10 nm or less, 50 nm or less, 100 nm or less, 200 nm or less, 500 nm or less, 800 nm or less, 1000 nm or less, 2000 nm or less, 3000 nm or less, 5000 nm or less, 10 microns or less, 20 microns or less, 30 microns or less, 50 microns or less, 100 microns or less, 150 microns or less, 200 microns or less, 300 microns or less, 500 microns or less, 800 microns or less, 1 mm or less, 2 mm or less, 4 mm or less, or in a range between any two of the values.

F8. The device or method of any prior embodiment, wherein the spacing between the two nearest pillars of the plurality of elements is in the range from 2 nm to less than 500 microns.

F9. The device or method of any prior embodiment, wherein the sample comprises whole blood or fractionated blood.

F10. The device or method of any prior embodiment, wherein the sample comprises any or a combination of a group, consisting of amniotic fluid, aqueous humour, vitreous humour, breast milk, cerebrospinal fluid (CSF), cerumen (earwax), chyle, chime, endolymph, perilymph, feces, gastric acid, gastric juice, lymph, mucus, nasal drainage, phlegm), pericardial fluid, peritoneal fluid, pleural fluid, pus, rheum, sebum, semen, sputum, sweat, synovial fluid, tears, vomit and exhaled condensate.

F11. The method of any prior embodiment, comprising converting a sample containing at least one target lysing component from non-liquid phase into liquid phase before step (i).

F12. The device or method of any prior embodiment, wherein at least one target lysing component in the sample proliferates on at least one of the two plates on which the cell-sample is deposited.

F13. The device or method of any prior embodiment, wherein the target percentage is 5% or less, 10% or less, 20% or less, 30% or less, 40% or less, 50% or less, 60% or less, 70% or less, 80% or less, 90% or less, 95% or less, 98% or less, 99% or less, 100% or less, or any value in a range between any two of these numbers.

F14. The device or method of any prior embodiment, wherein the substantial fraction is at least 51%, 60%, 70%, 80%, 90%, 95% or 99%

F15. The device or method of any prior embodiment, wherein the area of the highly uniform layer is equal to or larger than 0.1 mm$^2$, 0.5 mm$^2$, 1 mm$^2$, 3 mm$^2$, 5 mm$^2$, 10 mm$^2$, 20 mm$^2$, 50 mm$^2$, 70 mm$^2$, 100 mm$^2$, 200 mm$^2$, 500 mm$^2$, 800 mm$^2$, 1000 mm$^2$, 2000 mm$^2$, 5000 mm$^2$, 10000 mm$^2$, 20000 mm$^2$, 50000 mm$^2$, or 100000 mm$^2$; or in a range between any of the two values.

F16. The device or method of any prior embodiment, wherein on one or both the sample contact areas, the respective plate further comprises a layer of a reagent.

F17. The device or method of any prior embodiment, wherein the area of the first sample contact area or the second sample contact area is equal to or larger than 0.1 mm$^2$, 0.5 mm$^2$, 1 mm$^2$, 3 mm$^2$, 5 mm$^2$, 10 mm$^2$, 20 mm$^2$, 50 mm$^2$, 70 mm$^2$, 100 mm$^2$, 200 mm$^2$, 500 mm$^2$, 800 mm$^2$, 1000 mm$^2$, 2000 mm$^2$, 5000 mm$^2$, 10000 mm$^2$, 20000 mm$^2$, 50000 mm$^2$, or 100000 mm$^2$; or in a range between any of the two values.

F18. The method of any prior embodiment, where the compressing force is applied by a human hand.

F19. The method of any prior embodiment, where the compressing force is applied through a gas or fluid pressure.

G1. The device or method of any prior embodiment, wherein the pillars have:
  i. a shape of pillar with substantially uniform cross-section and a flat top surface;
  ii. a ratio of the width to the height equal or larger than one;
  iii. a filling factor of equal to 1% or larger; and
  iv. a product of the filling factor and the Young's modulus of the spacer is 2 MPa or larger,
  wherein the filling factor is the ratio of the spacer contact area to the total plate area.

G2. The device or method of any prior embodiment, wherein an average value of the uniform thickness of the layer is substantially the same as the uniform height of the spacer with a variation of less than 10%.

G3. The device or method of any prior embodiment, wherein the sample further comprises a second target lysing component.

G4. The device or method of any prior embodiment, wherein in the closed configuration at least 90% of the target lysing component is lysed and at least 90% of the non-target lysing component is lysed.

G5. The device or method of any prior embodiment, wherein in the closed configuration at least 99% of the target lysing component is lysed and at least 99% of the non-target lysing component is lysed.

G6. The device or method of any prior embodiment, wherein in the closed configuration at least 90% of the all target lysing components lysed and at least 90% of the non-target lysing component is lysed.

G7. The device or method of any prior embodiment, wherein the variation of the layer of uniform thickness is less than 30 nm.

G8. The device or method of any prior embodiment, wherein the layer of uniform thickness sample has a thickness uniformity of up to +/−5%.

G8. The device or method of any prior embodiment, wherein the pillars have a cross-sectional shape selected from round, polygonal, circular, square, rectangular, oval, elliptical, or any combination of the same.

G9. The device or method of any prior embodiment, wherein analyzing the non-target component comprises counting the number of the non-lysing-target analyte and calculating the concentration of the non-target component.

G10. The device or method of any prior embodiment, wherein the pillars have:
  i. a shape of pillar with substantially uniform cross-section and a flat top surface;
  ii. a ratio of the width to the height equal or larger than one;
  iii. a predetermined constant inter-spacer distance that is in the range of 10 □m to 200 □m;
  iv. a filling factor of equal to 1% or larger; and
  v. a product of the filling factor and the Young's modulus of the spacer is 2 MPa or larger.
  wherein the filling factor is the ratio of the spacer contact area to a total plate area.

G10. The device or method of any prior embodiment, wherein pressing the plates into the closed configuration is conducted either in parallel or sequentially, the parallel pressing applies an external force on an intended area at the same time, and the sequential pressing applies an external force on a part of an intended area and gradually move to other area.

G11. The device or method of any prior embodiment, wherein the blood sample is stained before being analyzed.

G12. The device or method of any prior embodiment, wherein the blood sample is stained with acridine orange (AO).

G13. The device or method of any prior embodiment, wherein a staining reagent is coated on at least one sample contact area, and the blood sample is stained with the staining reagent.

G14. The device or method of any prior embodiment, wherein the blood sample is analyzed by:
  i. illuminating at least part of the blood sample in the layer of uniform thickness;
  ii. obtaining one or more images of the cells using a CCD or CMOS sensor;
  iii. identifying the platelets in the image using a computer; and
  iv. counting a number of platelets in an area of the image.

G15. The device or method of any prior embodiment, wherein the layer of uniform thickness sample has a thickness uniformity of up to +/−5%.

G16. The device or method of any prior embodiment, wherein one or both of the plates comprise, on the respective sample contact area, a detection agent capable of selectively binding a target analyte in the sample.

G17. The device or method of any prior embodiment, wherein one or both of the plates comprise, on the respective sample contact area, a capture agent capable of selectively binding and immobilizing a target analyte in the sample.

G18. The method of any prior embodiment, further comprising: incubating an assay of the sample when the two plates are in the closed configuration.

Related Documents and Additional Examples

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu L$, also "uL" herein) or less, 500 $\mu L$ or less, 300 $\mu L$ or less, 250 $\mu L$ or less, 200 $\mu L$ or less, 170 $\mu L$ or less, 150 $\mu L$ or less, 125 $\mu L$ or less, 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 $\mu L$ or less, 1 $\mu L$ or less, or a range between any two of the values.

In some embodiments, the volume of the sample includes, but is not limited to, about 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values. In some embodiments, the volume of the sample includes, but is not limited to, about 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456,522, 62/456,598, 62/456,603, and 62/456,628, which were filed on Feb. 8, 2017, U.S. Provisional Application No. 62/459,276, 62/456,904, 62/457,075, and 62/457,009, which were filed on Feb. 9, 2017, and U.S. Provisional Application No. 62/459,303, 62/459,337, and 62/459,598, which were filed on Feb. 15, 2017, and U.S. Provisional Application No. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propionic acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAM RA); tetramethyl rhodamine; tetramethyl hodamine isothiocyanate (TRITC); riboflavin; 5-(2'-aminoethyl)aminonaphtha-lene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234, 538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
| --- | --- | --- |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values. |

-continued

| Parameters | Embodiments | Preferred Embodiments |
|---|---|---|
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 pm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm$^2$; or around 750 mm$^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
|---|---|---|
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |

-continued

| Parameters | Embodiments | Preferred Embodiments |
|---|---|---|
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 mm$^2$ (square millimeter) or less, 10 mm$^2$ or less, 25 mm$^2$ or less, 50 mm$^2$ or less, 75 mm$^2$ or less or in a range between any two of these values. | In the range of 10 to 150 mm$^2$; or about 50 mm$^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |

| Parameters | Embodiments | Preferred Embodiments |
| --- | --- | --- |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 $mm^2$ (square millimeter) or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The invention claimed is:

1. A device for analyzing an analyte in a sample, comprising:
   a first plate and a second plate, wherein:
   (i) the first and second plates are movable relative to each other into different configurations, including an open configuration and a closed configuration;
   (ii) the first plate comprises, on its inner surface, at least a first and a second sample contact areas, each contact area comprising spacers, wherein each spacer of the spacers in each of the at least first and second sample contact areas has a pillar shape and a bottom end fixed on the inner surface of the first plate and a top end that is distal to the first plate;
   (iii) the spacers in each of the at least first and second sample contact areas have a predetermined uniform height, wherein the predetermined uniform height of the spacers in the first sample contact area is different from that of the spacers in the second sample contact area;
   (iv) the at least first and second sample contact areas of the first plate are disposed at different depths along the inner surface of the first plate, so that the top ends of the spacers in the at least first and second sample contact areas are aligned on a same flat plane; and
   (v) the second plate comprises, on its inner surface, at least a first and a second sample contact areas that contact, respectively, in the closed configuration, the spacers in the at least first and the second sample contact areas of the first plate, wherein the at least first and second sample contact areas of the first and second plates are for contacting the sample that contains or is suspected of containing the analyte;
   wherein, in the open configuration, the first and second plates are partially or entirely separated apart, the spacing between the first and second plates is not regulated by the spacers, and the sample is deposited on one or both of the plates;
   wherein the closed configuration is configured after the sample deposition in the open configuration, and in the closed configuration: at least part of the deposited sample is confined by the two plates into a thin layer that has a respective uniform thickness over each of the at least first and second sample contact areas of the first plate, wherein the uniform thickness of the layer in the at least first and second sample contact areas of the first plate is different and is regulated by the plates and the spacers in the respective sample contact area of the first plate, and wherein, in the closed configuration, the at least first and the second sample contact areas of the first plate are fluidically connected.

2. The device of claim 1, wherein the predetermined uniform heights of the spacers in the first and second sample areas are in the range of 0.5 µm to 100 µm.

3. The device of claim 1, wherein the difference between the predetermined uniform heights of the spacers in the at least first and second sample contact areas is in the range of 0.5 µm to 100 µm.

4. The device of claim 1, wherein the difference between the predetermined uniform heights of the spacers in the at least first and second sample contact areas is in the range of 0.5 µm to 50 µm.

5. The device of claim 1, wherein the first and second plates are connected by a hinge and are movable relative to each other around the hinge.

6. The device of claim 1, wherein the spacers in the at least first and second sample areas have an inter-spacer distance that is periodic and in a range from 7 µm to 200 µm.

7. The device of claim 1, wherein the spacers in the first and second sample areas have an inter-spacer distance that is periodic and in a range from 50 µm to 150 µm.

8. The device of claim 1, wherein a separation between edges of the first and the second sample contact areas of each plate is from 20 µm to 1 mm.

9. The device of claim 1, wherein a separation between edges of the first and the second sample contact areas of each plate is from 100 to 500 µm.

10. The device of claim 1, wherein an average value of the uniform thickness of the layer in each sample contact area of the first plate is the same as the predetermined uniform height of the spacers therein with a variation of less than 10%.

11. The device of claim 1, wherein a height of one of the spacers in the at least first and second sample contact areas of the first and second plates is 5 µm.

12. The device of claim 1, wherein the first sample contact area of the first plate is next to the second sample contact area of the first plate.

13. The device of claim 1, wherein the spacers in the at least first and second sample contact areas of the first plate are arranged periodically.

14. The device of claim 1, further comprising a detector, wherein the detector measures a target analyte-related signal that is selected from the group consisting of:
   (i) luminescence selected from photoluminescence, electroluminescence, and electrochemiluminescence;
   (ii) light absorption, reflection, transmission, diffraction, scattering, or diffusion;
   (iii) surface Raman scattering;
   (iv) electrical impedance selected from resistance, capacitance, and inductance;
   (v) magnetic relaxivity; and
   (vi) any combination of (i)-(v).

15. The device of claim 1, wherein each of the first and second plates have a thickness of less than 200 µm.

16. The device of claim 1, wherein each of the first and second plates have a thickness of less than 100 µm.

17. The device of claim 1, wherein each of the plates has an area of less than 5 cm$^2$.

18. The device of claim 1, wherein at least one of the plates is partially or entirely transparent.

19. The device of claim 1, wherein at least one of the plates is made from a flexible polymer.

20. The device of claim 1, wherein at least one of the plates is a flexible plate, and the thickness of the flexible plate times the Young's modulus of the flexible plate is in the range of 60 to 75 GPa-µm.

21. The device of claim 1, wherein the spacers in the at least first and second sample contact areas of the first plate are spacers with a cross sectional shape selected from round, polygonal, circular, square, rectangular, oval, elliptical, or any combination of the same.

22. The device of claim 1, wherein the spacers in the at least first and second sample contact areas of the first plate have a flat top surface, wherein, for each spacer, the ratio of the lateral dimension of the spacer to its height is at least 1.

23. The device of claim 1, wherein each spacer of the spacers in the at least first and second sample contact areas of the first plate has a ratio of lateral dimension of the spacer to its height, and the ratio is at least 1.

24. The device of claim 1, wherein a height of one of the spacers in the at least first and second sample contact areas of the first plate is 30 µm.

25. The device of claim 1, wherein the spacers in the at least first and second sample contact areas of the first plate comprise sidewall corners that have a round shape with a radius of curvature at least 1 µm.

26. The device of claim 1, wherein the spacers in the at least first and second sample contact areas of the first plate have a density of at least 100/mm².

27. The device of claim 1, wherein
at least one of the plates is flexible,
for the flexible plate, the fourth power of the inter-spacer-distance (ISD) divided by the thickness of the flexible plate (h) and the Young's modulus (E) of the flexible plate, $ISD^4/(hE)$, is equal to or less than $5 \times 10^6$ um³/GPa, and
the thickness of the flexible plate times the Young's modulus of the flexible plate is in the range of 60 to 75 GPa-µm.

28. The device of claim 1, wherein
at least one of the plates is flexible;
for the flexible plate, the fourth power of the inter-spacer-distance (ISD) divided by the thickness of the flexible plate (h) and the Young's modulus (E) of the flexible plate, $ISD^4/(hE)$, is equal to or less than $10^6$ um³/GPa; and
the thickness of the flexible plate times the Young's modulus of the flexible plate is in the range of 60 to 75 GPa-µm.

29. The device of claim 1, wherein the first plate, the second plate, and the spacers in the at least first and second sample contact areas of the first plate each independently comprises polystyrene, poly(methyl methacrylate) (PMMB), polycarbonate (PC), cyclic olefin polymer (COP), cyclic olefin copolymer (COC), or another plastic.

30. The device of claim 1, wherein the analyte comprises a molecule, a protein, peptides, DNA, RNA, nucleic acid, cells, tissues, viruses, and/or nanoparticles with different shapes.

31. The device of claim 1, wherein at least one of the plates comprises a storage site in which assay reagents are stored.

32. The device of claim 1, wherein the first and the second sample contact areas of the first plate or the first and the second sample contact areas of the second plate are disposed between a pair of electrodes.

33. The device of claim 1, wherein each of the plates has an area of less than 2 cm².

34. The device of claim 1, wherein the sample comprises any or a combination of a group, consisting of amniotic fluid, aqueous humour, vitreous humour, breast milk, cerebrospinal fluid (CSF), cerumen (earwax), chyle, chime, endolymph, perilymph, feces, gastric acid, gastric juice, lymph, mucus, nasal drainage, phlegm, pericardial fluid, peritoneal fluid, pleural fluid, pus, rheum, sebum, semen, sputum, sweat, synovial fluid, tears, vomit and exhaled condensate.

35. The device of claim 1, wherein the spacers in the at least first and second sample contact areas of the first plate are fabricated by a mold containing features that are fabricated by either (a) directly reactive ion etching or ion beam etched or (b) by a duplication or multiple duplication of the features that are reactive ion etched or ion beam etched.

36. The device of claim 1, wherein the device is analyzed using a camera of a smart phone.

37. An apparatus comprising: the device of claim 1; and a camera that images the device of claim 1.

38. The device of claim 1, wherein the predetermined different heights of the spacers are configured to reduce the Hook effect in detection of the analyte.

39. The device of claim 1, wherein the analyte comprises white blood cell, red blood cell, and platelets.

40. The device of claim 1, wherein a spacer of the spacers in the first sample area of the first plate has a height of 5 µm, and the analyte comprises white blood cell, red blood cell, and platelets.

41. The device of claim 1, further comprising a dry binding site comprising a capture agent on one or both plates.

42. The device of claim 1, further comprising a dry binding site comprising an antibody or nucleic acid immobilized on one or both plates.

43. The device of claim 1, further comprising a releasable dry reagent that comprises a labeled reagent on one or both plates.

44. The device of claim 1, further comprising a releasable dry reagent that comprises a fluorescently-labeled reagent on one or both plates.

45. The device of claim 1, further comprising a releasable dry reagent that comprises a cell stain on one or both plates.

46. The device of claim 1, further comprising a releasable dry reagent that comprises a cell lysing on one or both plates.

47. The device of claim 1, further comprising an optical detector that detects an optical signal.

48. The device of claim 1, further comprising an electric detector that detects electrical signal.

* * * * *